(12) United States Patent
Thomma et al.

(10) Patent No.: US 9,732,354 B2
(45) Date of Patent: Aug. 15, 2017

(54) PLANT RESISTANCE GENE

(71) Applicants: Wageningen Universiteit, Wageningen (NL); Stichting voor de Technische Wetenschappen, Utrecht (NL)

(72) Inventors: Bart Pierre Hélène Joseph Thomma, Arnhem (NL); Koste Abdissa Yadeta, Davis, CA (US)

(73) Assignees: Wageningen Universiteit, Wageningen (NL); Stichting Voor De Technische Wetenschappen, Utrecht (NL)

( * ) Notice: Subject to any disclaimer, the term of this patent is extended or adjusted under 35 U.S.C. 154(b) by 0 days.

(21) Appl. No.: 14/399,673

(22) PCT Filed: May 24, 2013

(86) PCT No.: PCT/NL2013/050377
§ 371 (c)(1),
(2) Date: Nov. 7, 2014

(87) PCT Pub. No.: WO2013/176548
PCT Pub. Date: Nov. 28, 2013

(65) Prior Publication Data
US 2015/0143574 A1    May 21, 2015

(30) Foreign Application Priority Data
May 25, 2012  (EP) ..................... 12169568

(51) Int. Cl.
*C12N 15/82*    (2006.01)
*C07K 14/415*    (2006.01)
*C07K 16/16*    (2006.01)
*C12Q 1/68*    (2006.01)

(52) U.S. Cl.
CPC ........ *C12N 15/8282* (2013.01); *C07K 14/415* (2013.01); *C07K 16/16* (2013.01); *C12N 15/8281* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

2008/0184386 A1    7/2008    Cao

FOREIGN PATENT DOCUMENTS

EP    1 033 405    9/2000
WO    2008/054890    5/2008

OTHER PUBLICATIONS

Written Opinion, PCT/NL2013/050377, 5 pages.
International Search Report, PCT/NL2013/050377 mailed Sep. 30, 2013, 3 pages.
EM_PL DQ487672 Arabidopsis thalina clone, May 23, 2006, 1 page.
Fradin et al. Interfamily Transfer of Tomato Vel Mediates *Verticillium* Resistance in Arabidopsis. Plant Physiology 156 (2011) 2255-2265.
Yadeta et al. The *Arabidopsis thaliana* DNA-Binding Protein AHL19 Mediates Verticillium Wilt Resistance. Molecular Plant-Microbe Interactions 24 (2011) 1582-1591.

*Primary Examiner* — Medina A Ibrahim
(74) *Attorney, Agent, or Firm* — Thompson Hine LLP

(57) ABSTRACT

The invention relates to a new gene that is able to provide plants with resistance against pathogens, more preferably *Verticillium, Ralstonia* or *Fusarium*. Said gene is typical for Brassicaceae and encodes for a proteins having a sequence as depicted in FIG. 7 or FIG. 2A. Also provided are methods for enhancing the pathogen resistance of plants, wherein said plants preferably are Brassicaceae, but wherein the resistance also is functional in other plants. Further provided are host cells with a nucleotide construct encoding said protein.

8 Claims, 31 Drawing Sheets

Fig. 1

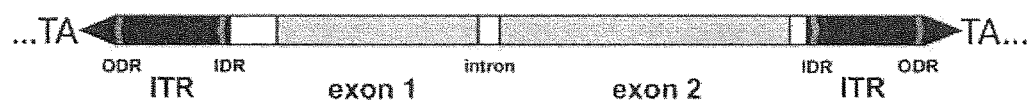

Fig. 2A

Figure 3A:
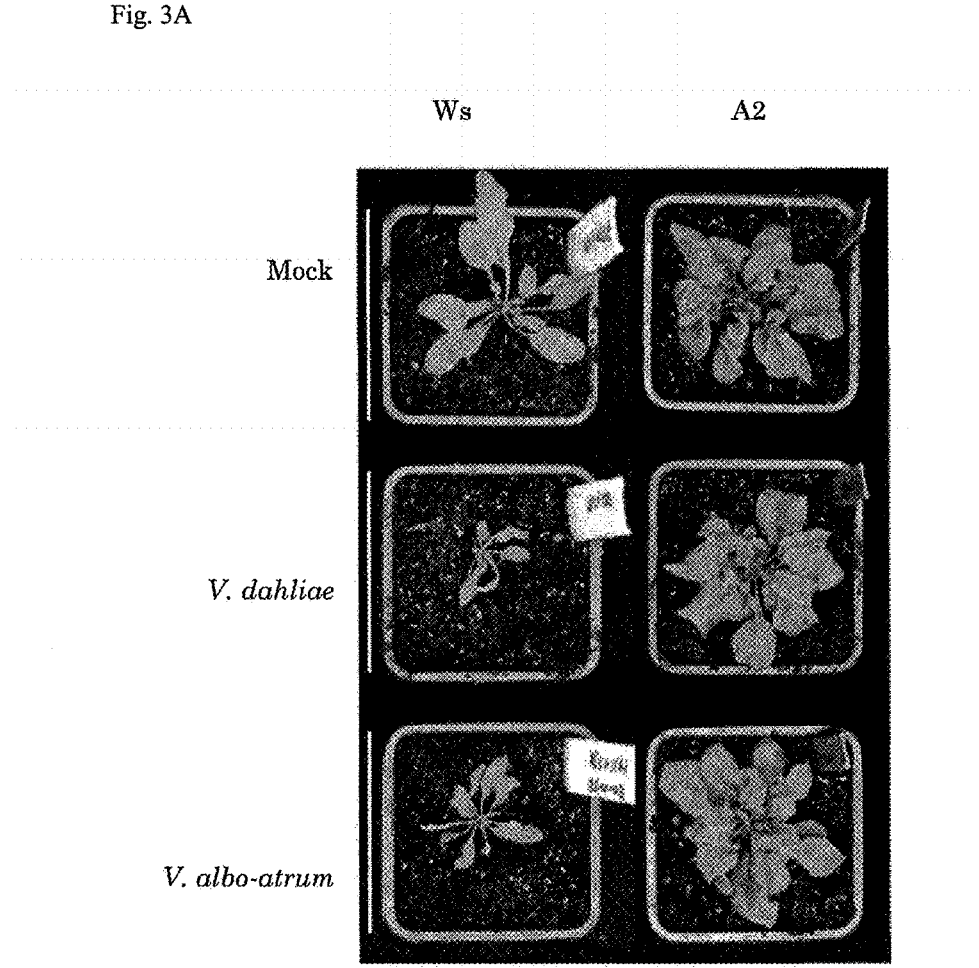
Figure 3B:
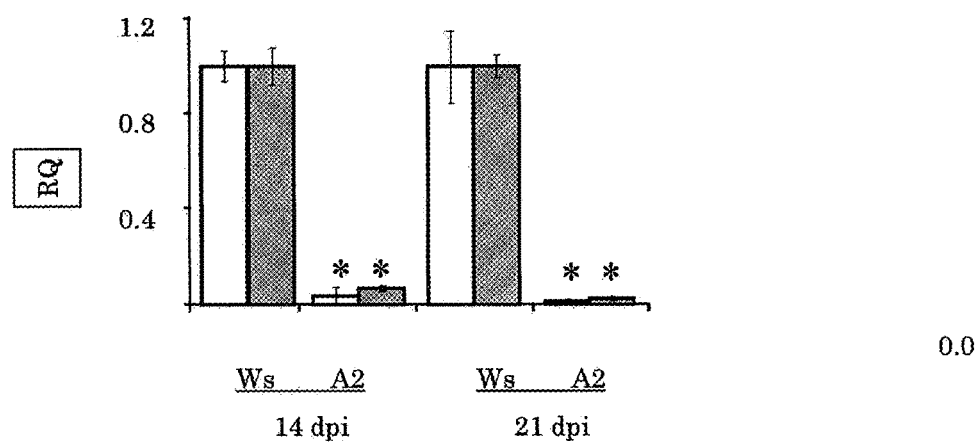
Figure 3C:
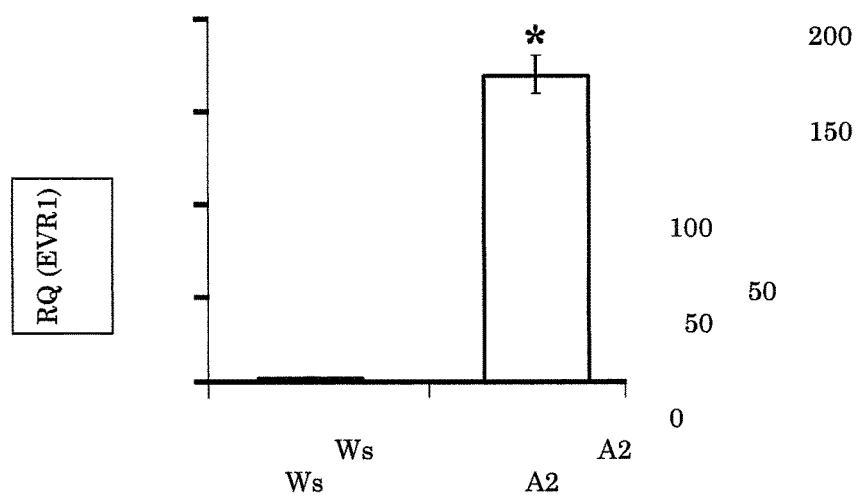
Figure 4A:
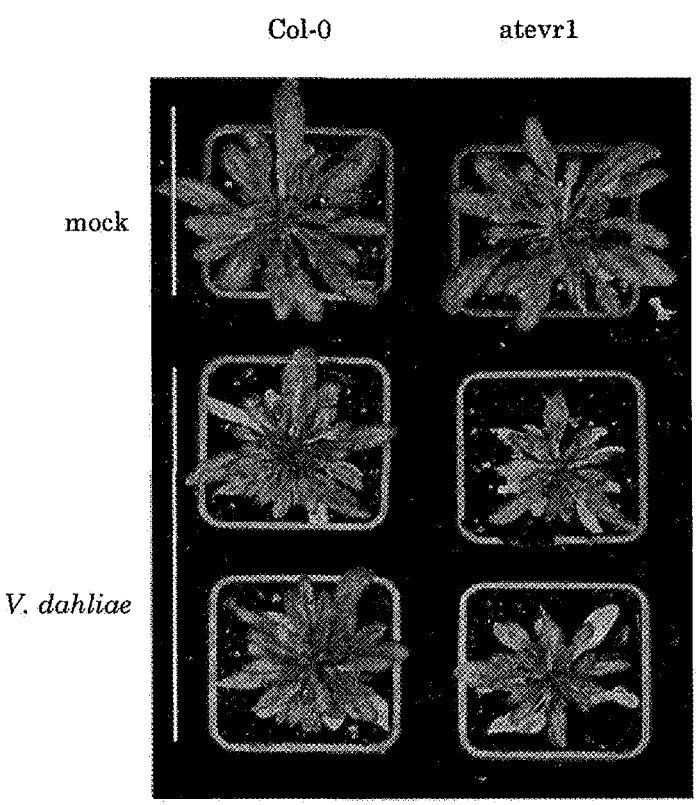
Figure 4B:
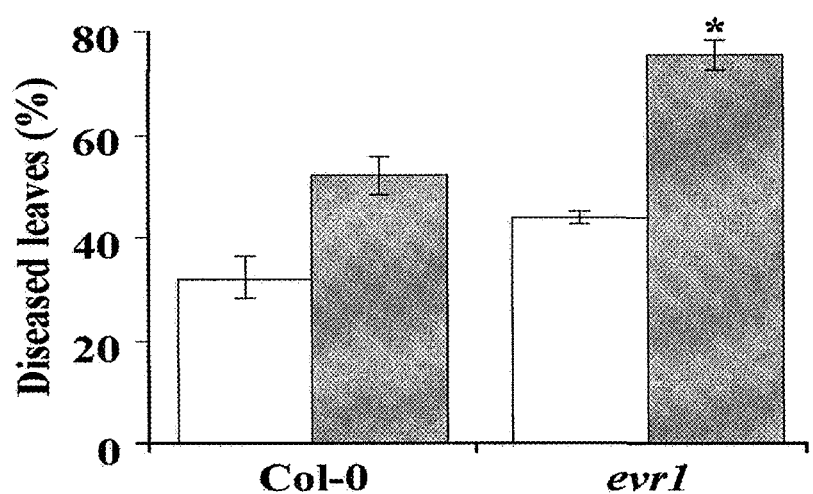
Figure 4C:
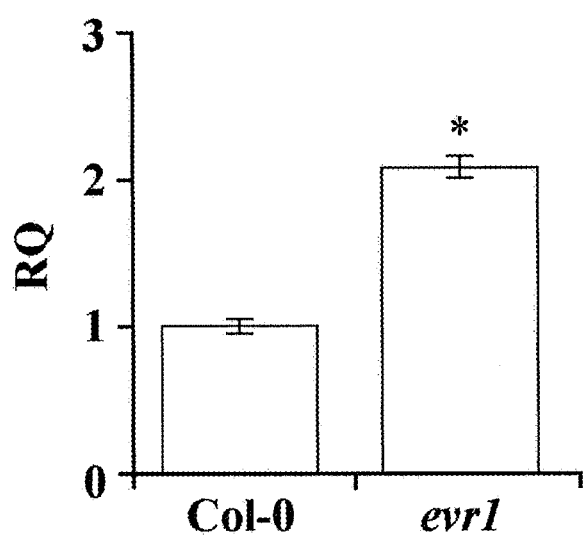
Figure 5A:
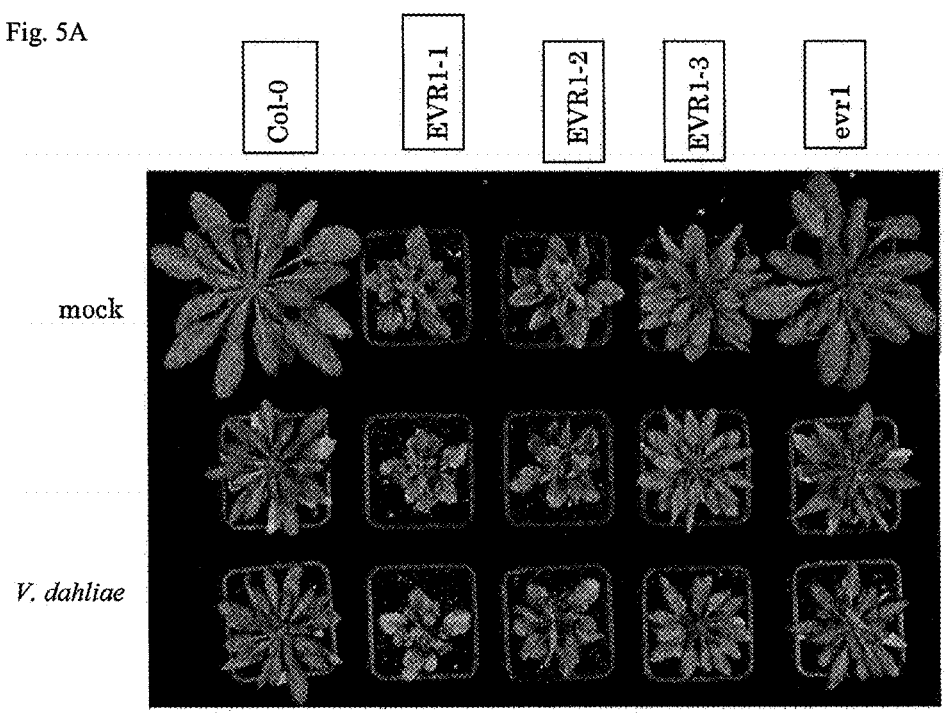
Figure 5B:
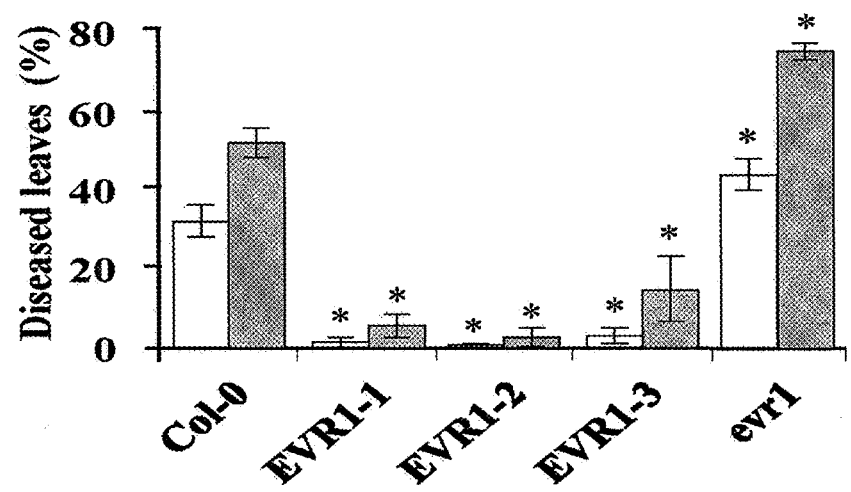
Figure 5C:
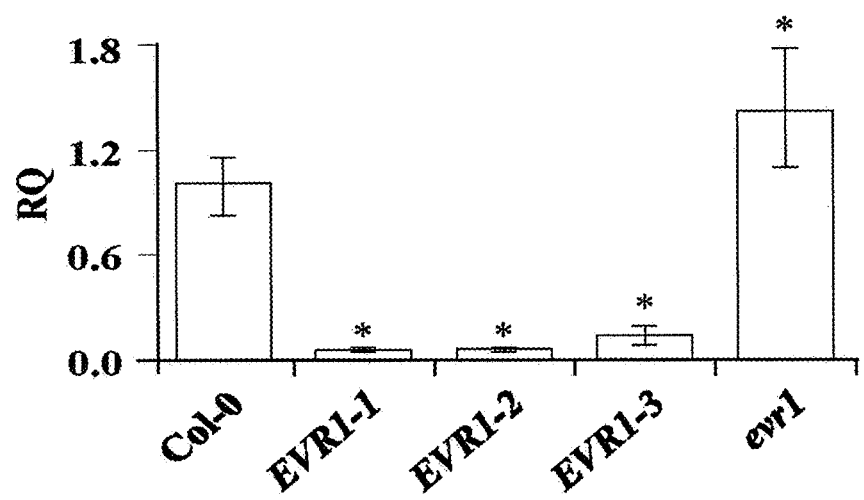
Figure 6A:
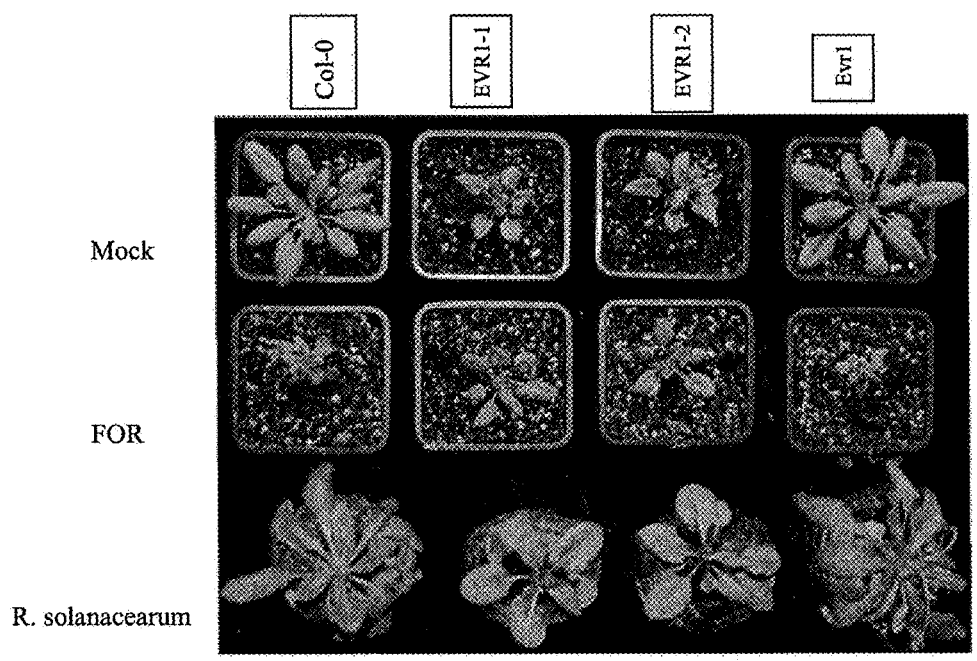
Figure 6B:
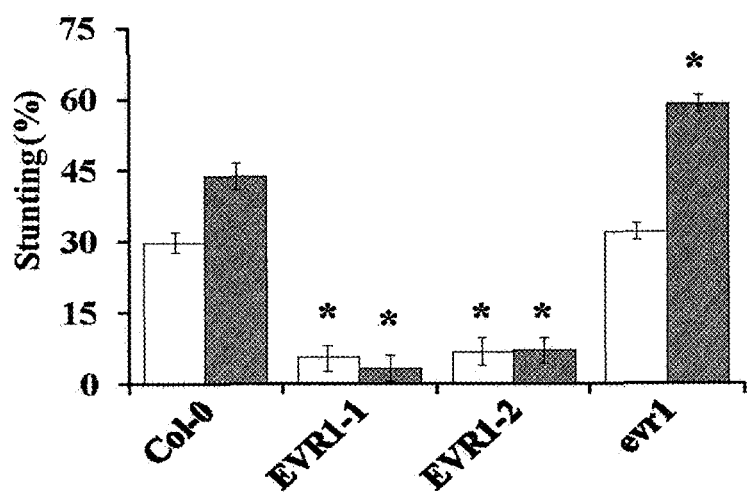
Figure 6C:
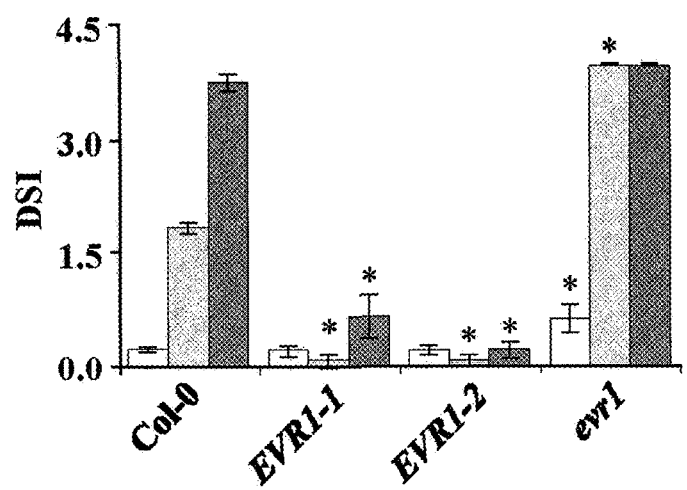
Figure 6D:
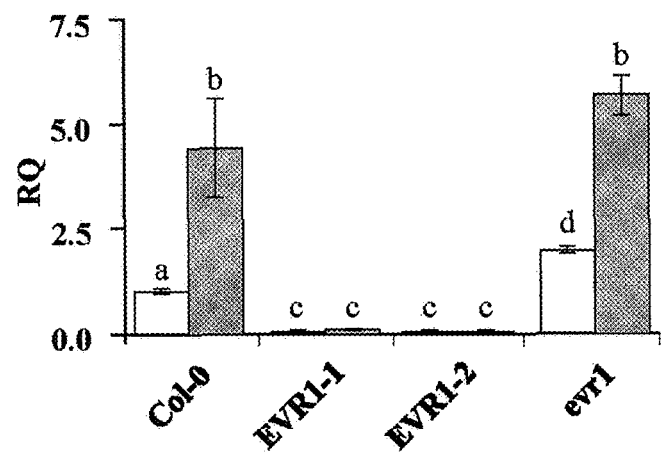
Figure 6E:
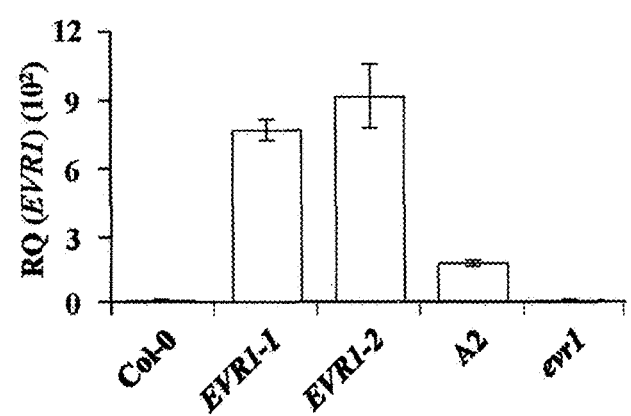
Figure 8A:
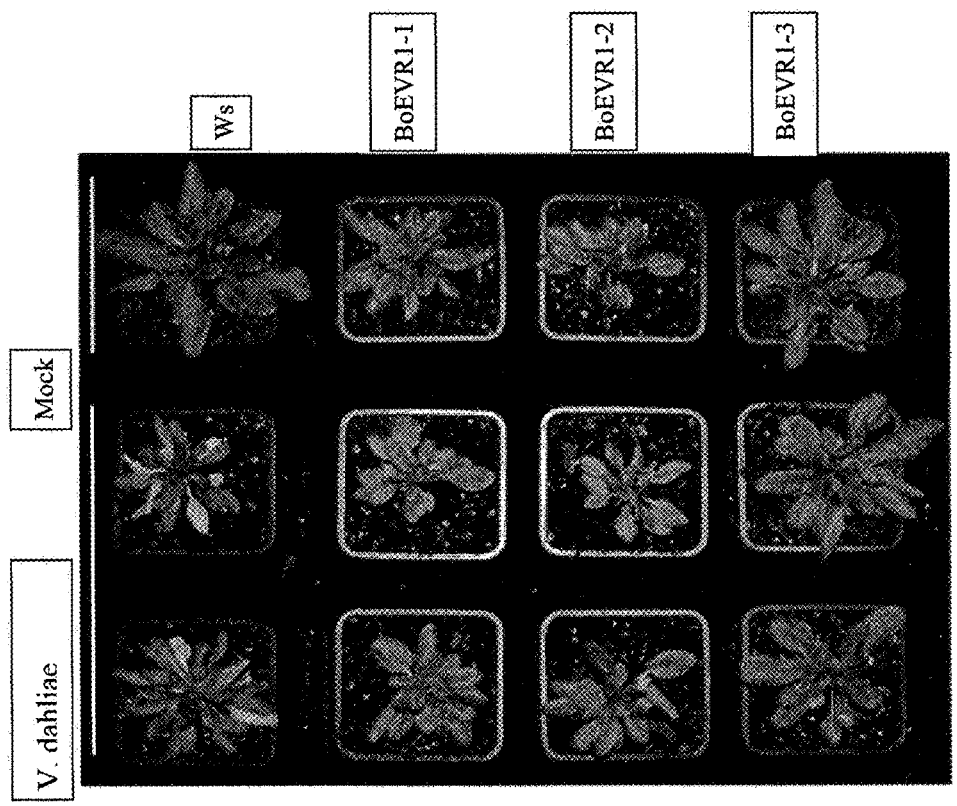
Figure 8B:
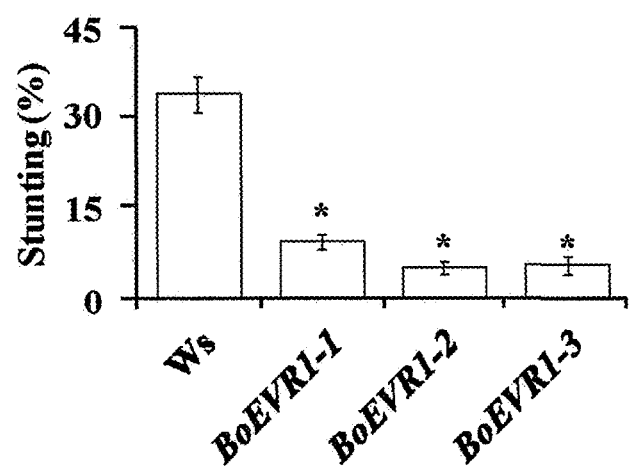
Figure 8C:
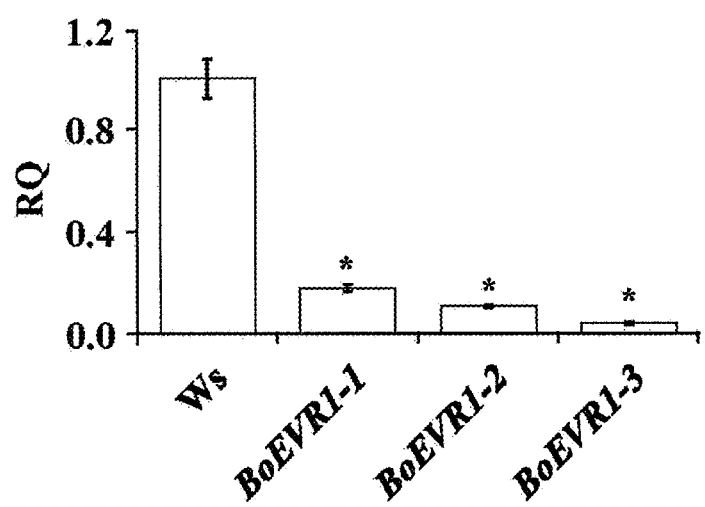
Figure 8D:
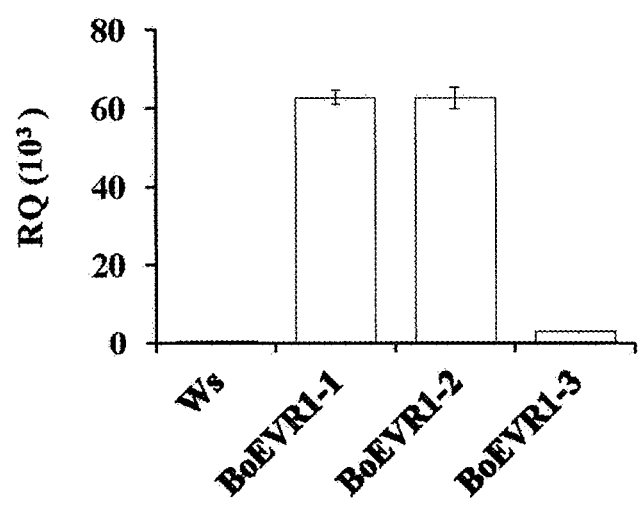
Figure 9A:
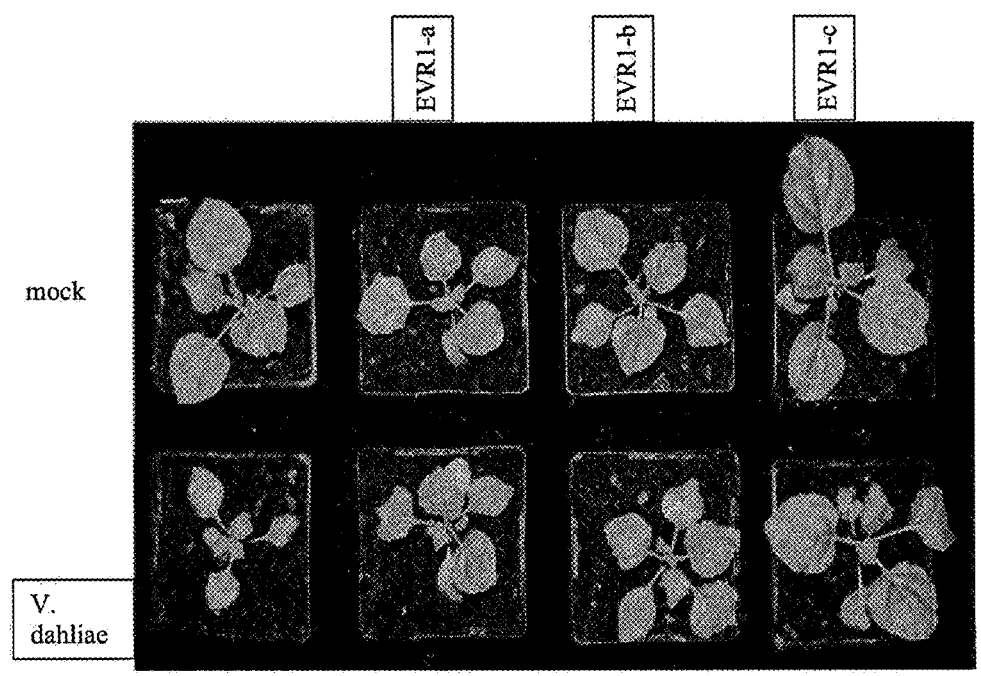
Figure 9B:
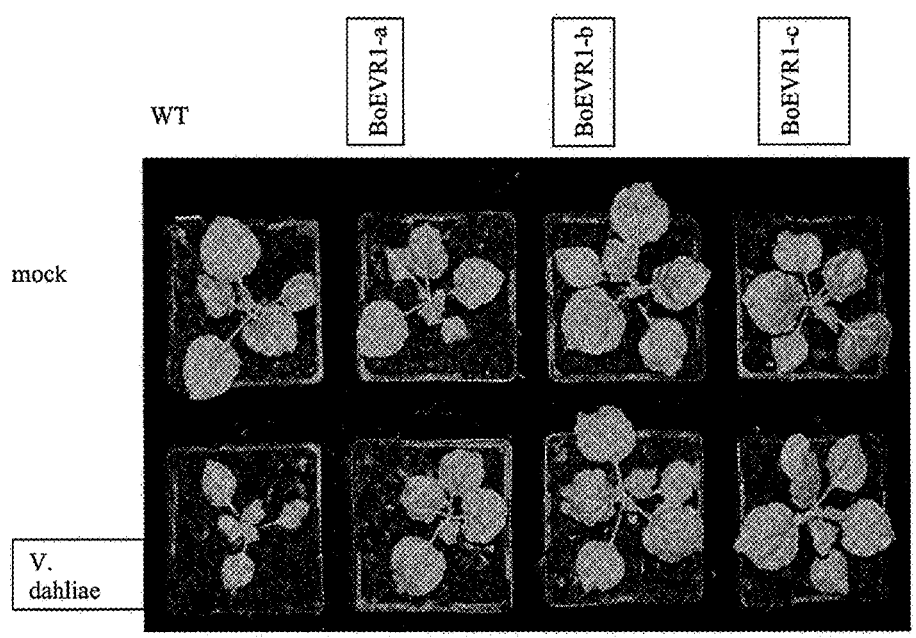
Figure 9C:
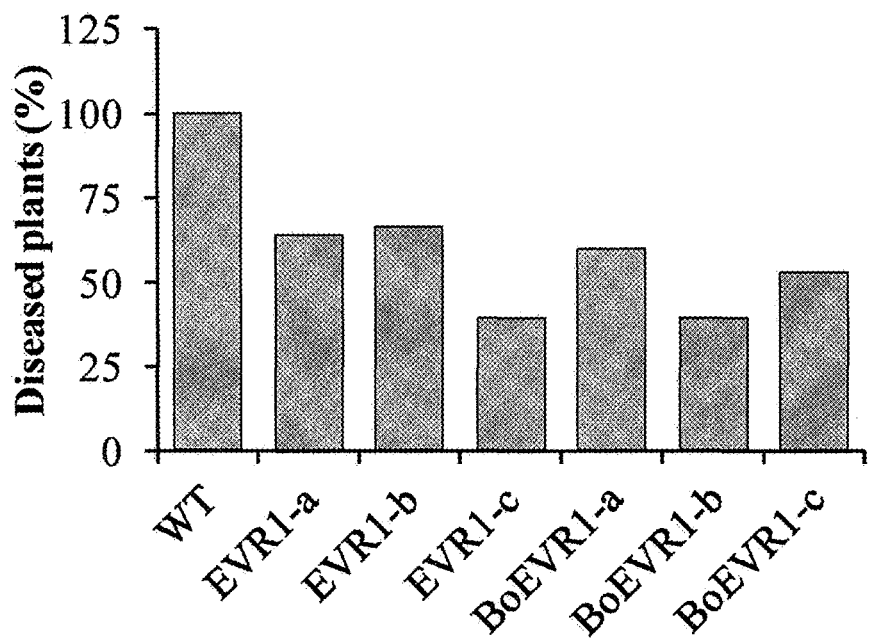
Figure 10:
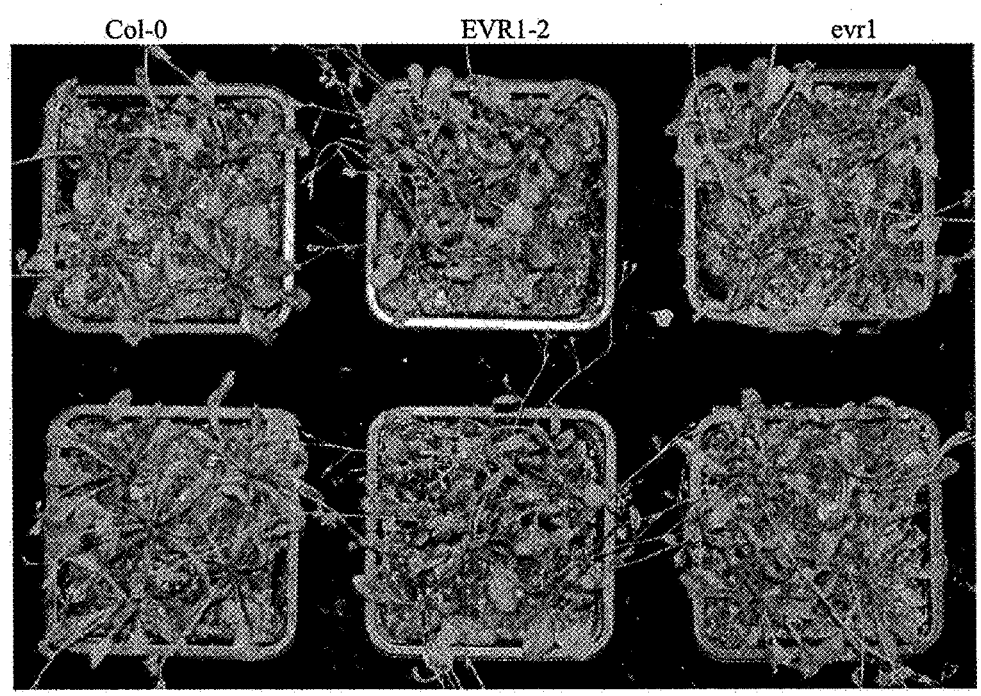
Figure 11:
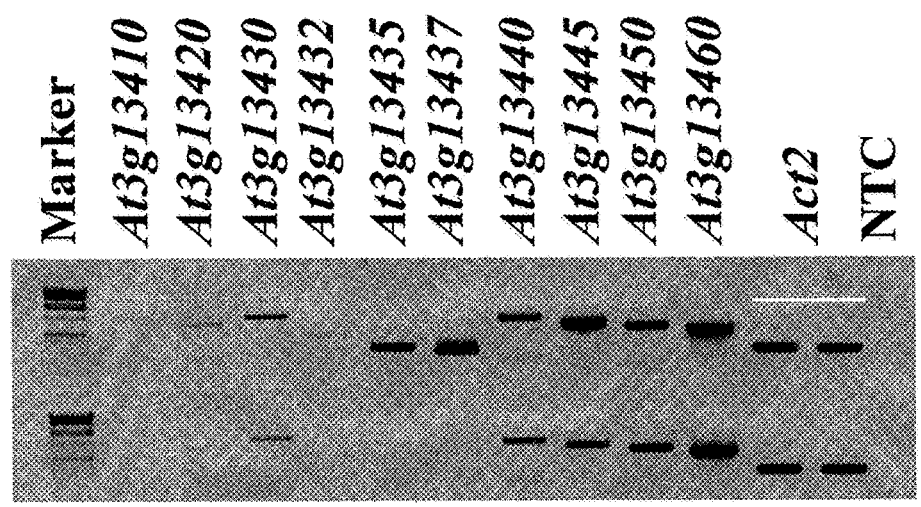
Figure 12A:
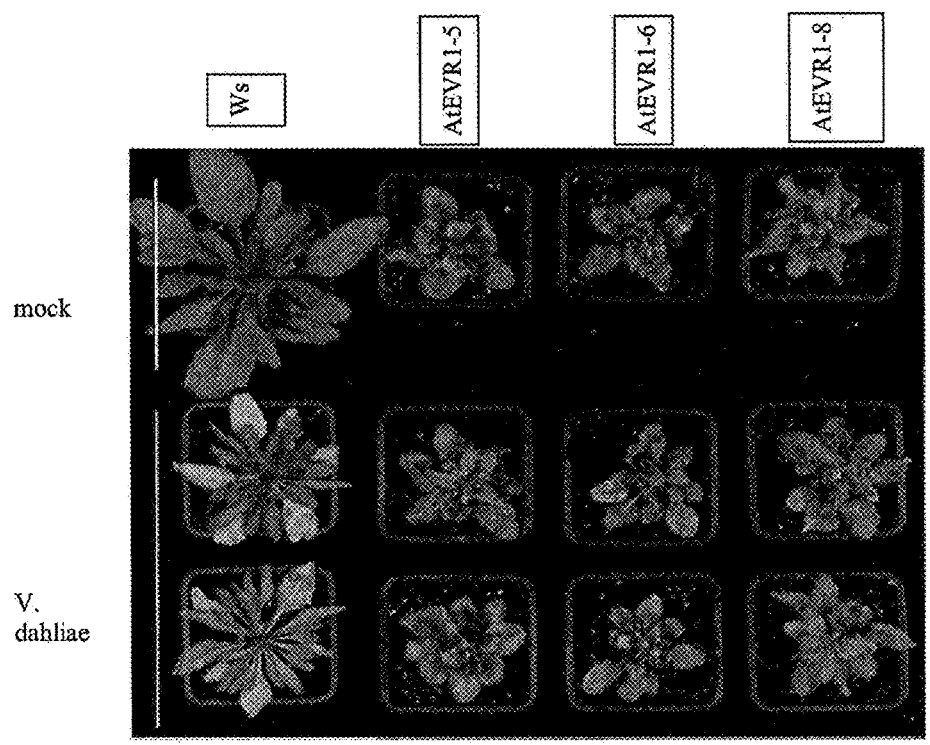
Figure 12B:
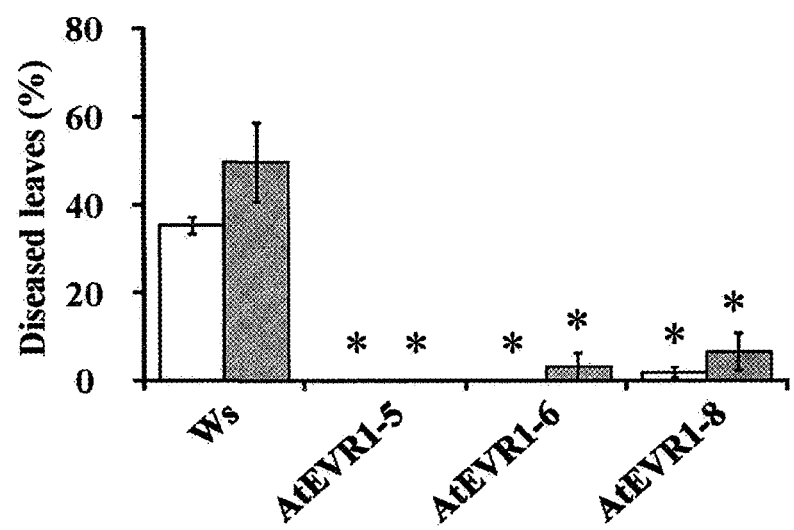
Figure 13:
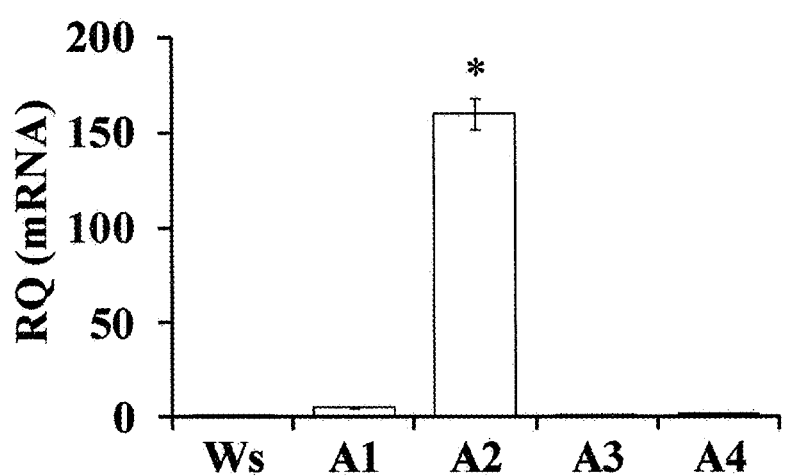
Figure 14:
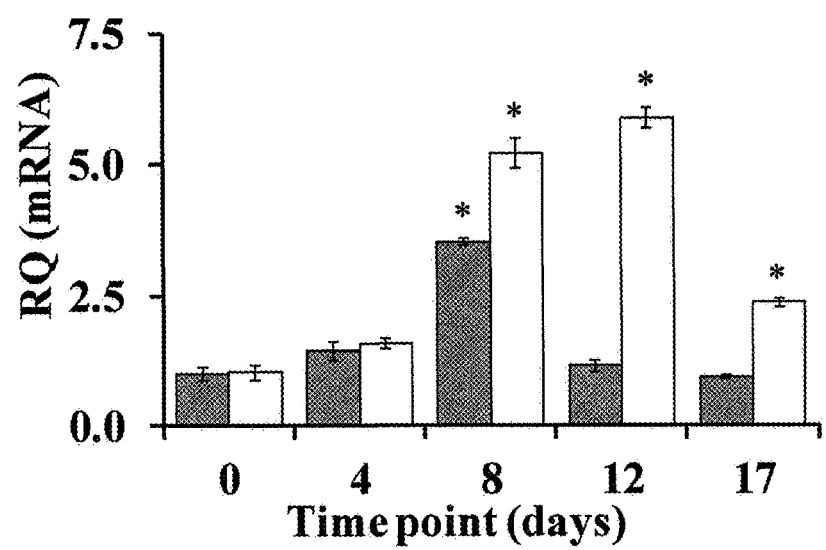
Figure 15:
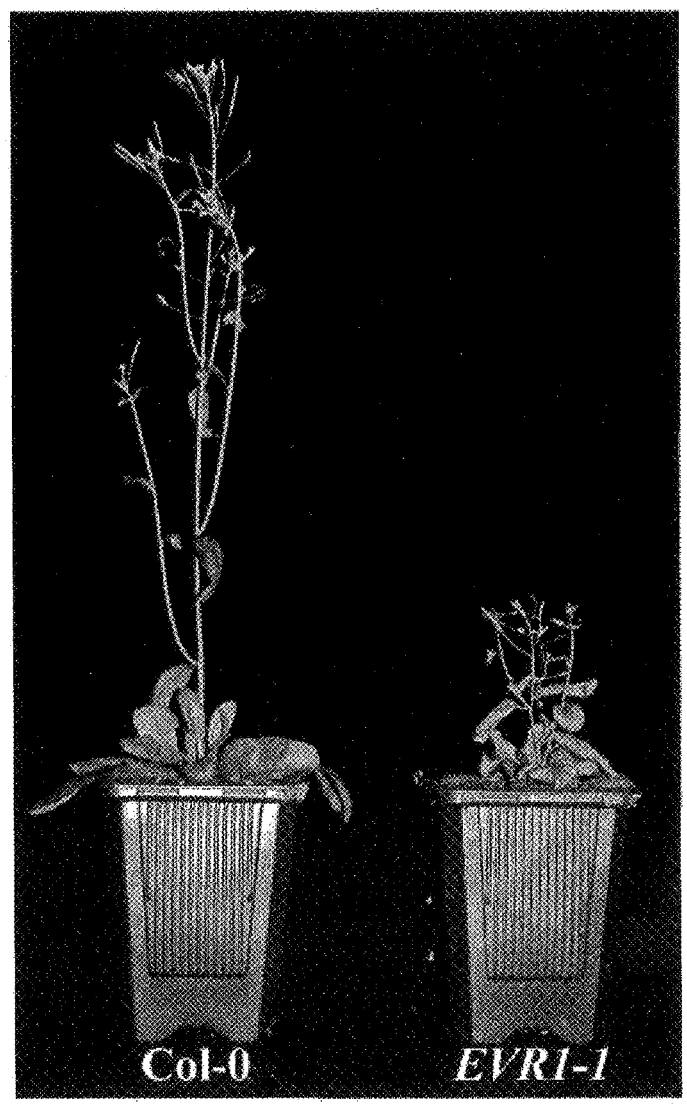
Figure 16:
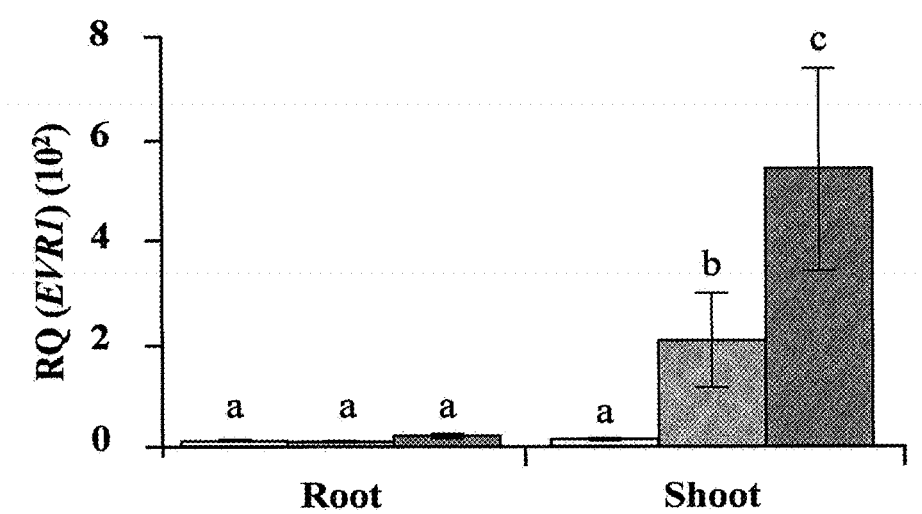

Amino acid sequence of EVR1 from *Arabidopsis thaliana*

```
  1 mslkfilial llllcitfsn stvvpfsknr kitneeeeee greidihkgk kitvkvsrsp
 61 pakgwiccnd
```

SEQ ID 2

Fig. 2B

Nucleotide sequence of EVR1 from *Arabidopsis thaliana*

```
  1 atgagtctca agttcattct tatagctttg cttctacttt tatgcatcac attttccaat
 61 tcgaccgtcg ttccttttc caaaaaccgg aaaattacca atgaagaaga agaagaagaa
121 ggtagagaga ttgacattca caaaggaaag aagatcaccg taaaagtcag ccgttcgcct
181 cctgcaaaag gctggatttg ttgcaatgat tga
```

SEQ ID 1

Fig. 7

AtEVR1 (SEQ ID NO: 1)
AlEVR1 (SEQ ID NO: 3)
BoEVR1 (SEQ ID NO: 4)
BrEVR1 (SEQ ID NO: 5)
SlEVR1 (SEQ ID No. 6)

PLANT RESISTANCE GENE

FIELD OF THE INVENTION

The invention relates to the field of plant pathology, more particular resistance to plant vascular diseases caused by fungal pathogens, more particularly *Verticillium, Fusarium* and *Ralstonia*. Further the invention relates to abiotic stress resistance, more particularly drought resistance.

BACKGROUND

*Verticillium* species belong to the phylum Ascomycota, which comprises the largest group of fungal (plant) pathogens. The genus *Verticillium* contains three major plant pathogenic species: *V. dahliae, V. albo-atrum,* and *V. longisporum* (Fradin and Thomma, 2006; Klosterman et al., 2009). While *V. dahliae* and *V. albo-atrum* infect over 200 plant species, *V. longisporum* is pathogenic mainly on Brassicaceae. The pathogens cause soil-borne vascular wilt, which is a devastating disease on many economically important crop species such as tomato, potato, cotton, and lettuce, but also on ornamental plants (Agrios, 2005; Fradin and Thomma, 2006; Klosterman et al., 2009). Controlling *Verticillium* wilt disease is difficult for several reasons: *Verticillium* produces resting structures that can survive in the soil for many years (Rowe and Powelson, 2002), it has a broad host range, and the fungus is difficult to be reached by fungicides once it has entered the xylem tissue. A commonly used control option, crop rotation, is mostly ineffective for controlling *Verticillium* wilt disease. Although soil fumigation is effective to control *Verticillium* wilt disease, use of soil fumigation is not appreciated due to the detrimental effects of the chemicals on public health and the environment. Soil fumigation is also not a preferred method for large scale field application. As a consequence, the preferred method to control *Verticillium* wilt disease is the use of genetic resistance.

Two distinct races (race 1 and race 2) have been described for *V. dahliae* and *V. albo-atrum* in tomato and lettuce (Fradin and Thomma, 2006; Klosterman et al., 2009). While resistance against race 1 strains has been identified in these two plant species (Schaible, 1951; Fradin et al., 2009; Hayes et al., 2011), no resistance against race 2 has been identified so far. Genetic resistance against *Verticillium* wilt diseases has also been reported for several other economically important crop species (Pegg, 2002). However, so far the only *Verticillium* resistance locus that has been cloned and functionally characterized is the tomato Ve locus that contains the Ve1 gene that provides resistance in tomato against race 1 isolates of *V. dahliae* and *V. albo-atrum* (Kawchuk et al., 2001; Fradin et al., 2009).

Recently, it has been shown that transgenic expression of Ve1 in *Arabidopsis* provides resistance against *Verticillium* race 1 isolates (Fradin et al., 2011). Over the years, *Arabidopsis* has increasingly been used as a model host for studying *Verticillium*-host interactions (Veronese et al., 2003; Tjamos et al., 2005; Fradin and Thomma, 2006; Johansson et al., 2006; Ellendorff et al., 2009; Pantelides et al., 2010b). In addition to screening germplasm for resistance (Schaible, 1951; Veronese et al., 2003), mutagenesis followed by screening for enhanced resistance with a pathogen of interest is a means to identify novel resistance traits. Several molecular techniques have been used to generate random mutants in *Arabidopsis*, such as EMS- and radiation-induced mutation, and transposon and activation tagging. Activation tagging involves the random integration of promoter or enhancer sequences in a genome, using either a T-DNA or a transposon, generally leading to enhanced expression of genes near the integration site and generating gain-of-function mutations (Weigel et al., 2000; Ayliffe and Pryor, 2007; Pereira and Marsch-Martinez, 2011). Insertion of enhancer sequences in the genome may positively regulate gene expression, even when inserted at a considerable distance to the target gene (Lewin, 2008). Some of the advantages of activation tagging over knock-out strategies include that activation tagging generates dominant instead of recessive mutations, it generates viable mutants for those genes where knock-outs would lead to lethal phenotypes and it is also applicable to dissect phenotypes of redundant genes (Pereira and Marsch-Martinez, 2011).

SUMMARY OF THE INVENTION

The inventors now have found a method for providing at least partial resistance or increasing resistance in a plant against pathogen infection comprising providing a plant or a part thereof with a nucleic acid encoding the amino acid sequence EVR1 of FIG. 2A or a functional fragment or a functional homologue thereof, preferably wherein said plant is a plant from the Brassicaceae or Solanaceae family. In said method said pathogen infection comprises *Verticillium, Fusarium* and/or *Ralstonia* infection, preferably *Verticillium dahliae, Verticillium alboatrum, Verticillium longisporum, Fusarium oxysporum* or *Ralstonia solanocearum* infection. Preferably, in said method the functional homologue is selected from the group of amino acid sequences consisting of the sequences encoded by the nucleic acid sequences depicted in FIG. 7.

Figure 7:
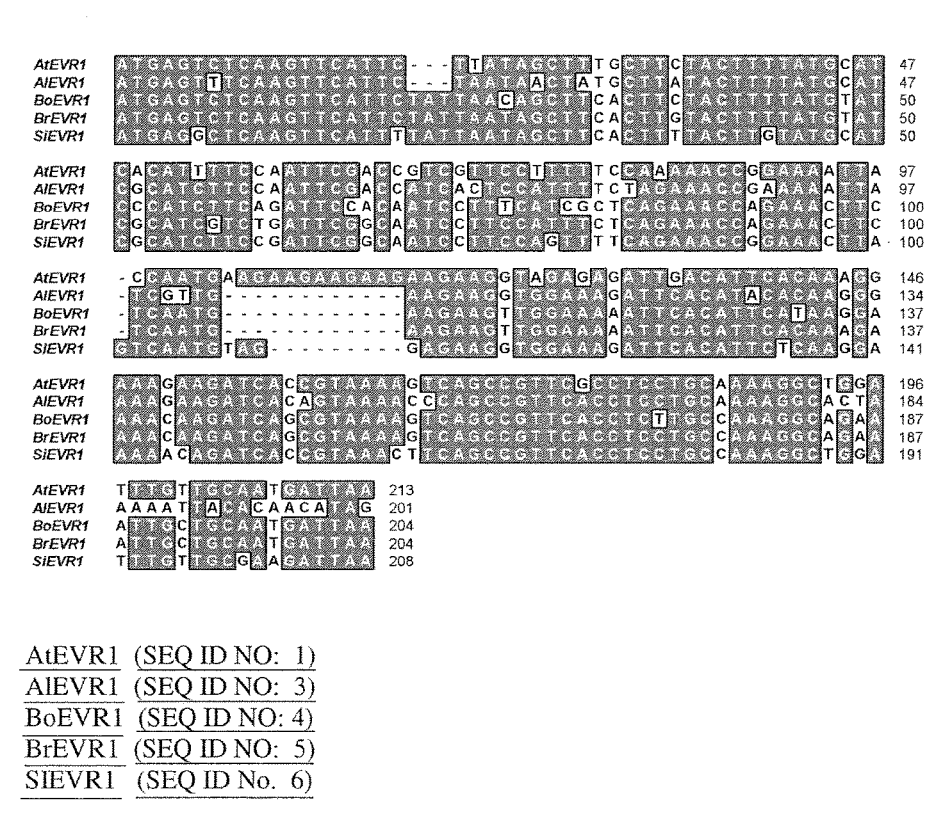

In another preferred embodiment the nucleic acid sequence as defined in claim 1 comprises a nucleic acid sequence as depicted in FIG. 2B or a nucleic acid sequence selected from the group of sequences depicted in FIG. 7.

Further part of the invention is a method for breeding a pathogen resistant plant, comprising
a. using the gametes of a first plant that already contains a nucleic acid sequence as defined above, wherein said step optionally comprises adapting the ploidy level of said gametes;
b. using said gametes in a cross with gametes of a second plant; and
c. selecting the offspring of said cross for the presence of said nucleic acid sequence.

Also part of the invention is a method for selecting a plant or plant material or progeny thereof for its susceptibility or resistance to a pathogen infection, said method comprising the steps of testing at least part of said plant or plant material or progeny thereof for the presence or absence of a nucleic acid as defined above.

The invention further relates to a marker for marker assisted selection in plant breeding to obtain pathogen resistance, wherein said marker is chosen from the markers EVR1H, BrF0, BrR1, BaF1, AsR1, MPR15F, MPR15R, dMRP15-F1, dMRP15-R1.

Further, the invention entails an isolated or recombinant nucleic acid sequence comprising a nucleic acid sequence encoding the amino acid sequence EVR1 of FIG. 2A or a functional fragment thereof, or a nucleic acid as depicted in FIG. 7 or a functional fragment thereof. In addition, the invention relates to a vector comprising a nucleic acid sequence according to claim 8. Preferably said vector further comprises the promoter and/or terminator to which the gene is naturally associated, more preferably a truncated promoter having less than 1000 nucleotides upstream of the gene sequence. In an alternative preferred embodiment the vector further comprises a pathogen inducible promoter, operably linked to the nucleic acid sequence of the invention.

The invention further comprises a transgenic host cell comprising a nucleic acid according to the invention or a vector according to the invention, wherein said host cell preferably is an *Agrobacterium* cell or a plant cell. Alternatively, the invention provides a transgenic host cell, preferably an *Agrobacterium* cell or a plant cell, comprising a chimeric gene, said chimeric gene comprising
  a. a plant-expressible promoter
  b. a DNA region encoding the amino acid sequence EVR2 of FIG. 2A or a functional fragment thereof, or a nucleic acid as depicted in FIG. 7 or a functional fragment thereof, and optionally
  c. a transcription termination and polyadenylation region functional in plant cells.

Also provided by the invention is a transgenic plant cell comprising a nucleic acid according to the invention or a vector according to the invention, or a chimeric gene as defined above, preferably wherein said plant cell is a cell from a Solanaceae or Brassicaceae plant.

The invention further entails a transgenic plant comprising a cell as defined above. Also comprised in the invention is a part derived from such a plant, wherein said part is selected from a seed, a fruit, a leaf, a stem or a tuber.

Further part of the invention is a protein encoded by an isolated or recombinant nucleic acid according to the invention or a functional fragment thereof, preferably wherein said protein has the amino acid sequence of EVR1 as depicted in FIG. 2A. The invention further comprises an antibody that specifically binds to a protein encoded by an isolated or recombinant nucleic acid or a functional fragment thereof, preferably wherein said protein has the amino acid sequence of EVR1 as depicted in FIG. 2A.

LEGENDS TO THE FIGURES

FIG. 1: Schematic representation of the full-length genomic DNA sequence of EVR1 gene.

FIG. 2: Amino acid (A) and nucleotide (B) sequence of EVR1 from *Arabidopsis thaliana.*

FIG. 3: The activation-tagged *Arabidopsis* mutant A2 is more resistant to *V. dahliae* and *V. albo-atrum*. (A) Typical symptoms of *Verticillium* on the wild-type (Ws) and the activation-tagged mutant A2. Picture was taken at 21 days post inoculation (dpi) and a representative of three independent experimental replicates is shown. (B) Relative quantification (RQ) by real-time PCR of *Verticillium* colonization by comparing levels of the *V. dahliae* (white bars) and *V. albo-atrum* (grey bars) internal transcribed spacer (ITS) region of the ribosomal DNA (as measure for fungal biomass) relative to levels of the large subunit of the *Arabidopsis* RubisCo gene (for equilibration) at 14 and 21 dpi. Bars represent averages with standard deviation of four technical replicates. A representative of three independent experiments is shown. (C) Relative quantification (RQ) of EVR1 transcription level in the wild-type Ws and the activation-tagged mutant A2. The bar represents the average of three independent experiments and standard deviation of the means and asterisks indicate significant differences (Dunnett t-test at P=0.01) compared to the wild-type Ws, FIG. 4: Knocking out EVR1 enhances *Arabidopsis* susceptibility to *Verticillium* wilt. (A) Typical symptoms of *V. dahliae* on the wild-type (Col-0) and EVR1 knock out (evr1) plants. Picture was taken at 21 days post inoculation (dpi) and a representative of three independent experimental replicates is shown. (B) Disease severity score for the wild-type (Col-0) and evr1 at 14 (white bar) and 21 (grey bar) days post inoculation (dpi). The total number of rosette leaves and the number of rosette leaves that showed *Verticillium* symptoms were counted at least from eight plants and percentage of the diseased leaves were calculated as an indication of disease severity. The bars represent averages of three independent experiments with standard deviation and asterisks indicate significance differences (Dunnett t-test at P=0.05). (C) Relative quantification (RQ) by real-time PCR of *Verticillium* colonization by comparing levels of the *V. dahliae* internal transcribed spacer (ITS) region of the ribosomal DNA (as measure for fungal biomass) relative to levels of the large subunit of the *Arabidopsis* RubisCo gene (for equilibration) at 21 dpi. Bars represent averages with standard deviation of four technical replicates. A representative of three independent experiments is shown.

FIG. 5: EVR1 over-expressing *Arabidopsis* plants are resistant to *V. dahliae*. (A) Typical symptoms of *V. dahliae* on the wild-type (Col-0), three EVR1 expressing lines (EVR1-1, EVR1-2, and EVR1-3) and EVR1 knock out line (evr1). Picture was taken at 21 days post inoculation and a representative of three experimental replicates is shown. (B) Disease severity score for the wild-type (Col-0), the three EVR1 expressing lines (EVR1-1, EVR1-2, and EVR1-3) and EVR1 knock out line (earl) at 14 (white bar) and 21 (grey bar) days post inoculation (dpi). The total number of rosette leaves and the number of rosette leaves that showed *Verticillium* symptoms were counted at least from eight plants and percentage of the diseased leaves were calculated as an indication of disease severity. The bars represent the average of three independent experiments with standard deviation and asterisks indicate significance differences (Dunnett t-test at P=0.05). (C) Relative quantification (RQ) by real-time PCR of *Verticillium* colonization by comparing levels of the *V. dahliae* internal transcribed spacer (ITS) region of the ribosomal DNA (as measure for fungal biomass) relative to levels of the large subunit of the *Arabidopsis* RubisCo gene (for equilibration) at 21 dpi. Bars represent averages with standard deviation of four technical replicates. A representative of three independent experiments is shown.

FIG. 6: EVR1 over-expression provides resistance to other vascular wilt pathogens. (A). typical disease symptoms caused by *Fusarium oxysporum* f.sp. *raphani* and *R. solanacearum* on the wild-type (Col-0), two EVR1 expressing plants (EVR1-1 and EVR1-2) and the EVR1 knock out line (evr1) at 12 (*F. oxysporum*) and 5 (*R. solanacearum*) days post inoculation (dpi). The experiment was repeated at least three times and representative of the three replications is shown. (B) *Fusarium*-induced stunting of wild-type (Col-0) plants, two independent EVR1 over-expression lines (EVR1-1 and, EVR1-2) and of the EVR1 knockout line (evr1) at 10 and 14 dpi. Rosette diameters of inoculated plants were compared with those of mock-inoculated plants. The bars represent averages of two independent experiments with standard deviation and asterisks indicate significant differences (Dunnett t-test at P=0.05). (C) Disease severity index (DSI) scores upon inoculation of at least 21 plants with *R. solanacearum* on a scale of 0 (no infection) to 4 (all rosette leaves diseased) at 3 (white bar), 6 (light grey bar) and 10 (dark grey bar) dpi. Bars represent averages with standard deviation of three independent biological replicates and asterisks indicate significant differences (p=0.05). (D) Relative quantification (RQ) by real-time PCR of *R. solanacearum* colonization in wild-type (Col-0), two independent EVR1 over-expressing lines (EVR1-1 and, EVR1-2), and of the EVR1 knockout line (earl) by comparing levels of the *R. solanacearum* endoglucanase gene (as measure for *Ralstonia* biomass) relative to levels of the large subunit of the *Arabidopsis* RubisCo gene (for equilibration) at 3 and 5 dpi. Bars represent averages with standard deviation of four technical replicates and a representative of three independent experiments is shown. (E) Relative quantification (RQ) of EVR1 transcription in wild-type (Col-0) plants, two independent EVR1 over-expressing plants (EVR1-1 and EVR1-2) and of the EVR1 knock out line (evr1). Bars represent averages with standard deviation of three biological replicates.

FIG. 7: EVR1 is highly conserved in Brassicaceae family. Nucleotide sequence alignment of *Arabidopsis thaliana* EVR1 (AtEVR1) and its homologs from *Arabidopsis lyrata* (AlEVR1), *Brassica oleracea* var. *gemmifera* (BoEVR1), *Brassica rapa* (BrEVR1) and *Sisymbrium irio* (SiEVR1).

FIG. 8: BoEVR1 over-expression enhances *Arabidopsis* resistance to *Verticillium* wilt. (A). Typical disease symptoms caused by *V. dahliae* on the wild-type (Ws) and three independent BoEVR1 over-expressing plants (BoEVR1-1, BoEVR1-2 and BoEVR1-3) at 21 days post inoculation (dpi). The experiment was repeated at least three times and representative of the three independent biological replications is shown. (B) *Verticillium*-induced stunting of wild-type (Ws), three independent BoEVR1 over-expressing plants (BoEVR1-1, BoEVR1-2 and BoEVR1-3) at 21 dpi. Rosette diameters of inoculated plants were compared with those of mock-inoculated plants. The bars represent averages of three independent experiments with standard deviation and asterisks indicate significant differences (Dunnett t-test at P=0.05). (C) Relative quantification (RQ) by real-time PCR of *Verticillium* colonization by comparing levels of the *V. dahliae* internal transcribed spacer (ITS) region of the ribosomal DNA (as measure for fungal biomass) relative to levels of the large subunit of the *Arabidopsis* RubisCo gene (for equilibration) at 21 dpi. Bars represent averages with standard deviation of four technical replicates. A representative of three independent experiments is shown. (D) Relative quantification (RQ) of EVR1 transcription in wild-type (Ws) and three independent BoEVR1 over-expressing plants (BoEVR1-1 and BoEVR1-2, and BoEVR1-3). Bars represent averages with standard deviation of three biological replicates FIG. 9: AtEVR1 or BoEVR1 over-expression in *N. benthamiana* results in resistance to *V. dahliae.*

Typical symptoms of *V. dahliae* on the wild-type (WT), AtEVR1 (EVR1-a, b, c) (A) and BoEVR1 (BoEVR1-a, b, c (B) over-expressing *N. benthamiana* plants. Pictures were made at 10 dpi and the upper and lower rows indicate mock- and *V. dahliae*-inoculated plants, respectively. C) Percentage of plants (n=20) that showed clear *Verticillium* symptoms at 10 dpi.

FIG. 10: EVR1 over-expressing plants are tolerant to drought stress. Three weeks-old wild-type Col-0, EVR1 expressing line (EVR1-1) and EVR1 knock out line (evr1) plants were exposed to drought stress and picture was taken at 14 days post drought treatment. The assay was repeated three times and a representative of the replicates is shown.

FIG. 11. Expression analysis of genes flanking the insertion site in the A2 mutant (top row) when compared to wild-type (bottom row) plants in absence of pathogen inoculation. The gene encoding EVR1 is denominated At3g13437. Reactions to amplify the Actin 2 gene and a non-template control (NTC) were included as controls.

FIG. 12. EVR1 over-expressing *Arabidopsis* plants are resistant to *V. dahliae*. (A) Typical symptoms of *V. dahliae* on the wild-type (Ws) and three independent EVR1 over-expressing lines in Ws background (EVR1-4, EVR1-5, and EVR1-6) at 21 days post inoculation (dpi). Representative of three experimental replicates is shown. (B) Disease severity score for the wild-type (Ws) and three independent EVR1 over-expressing lines in Ws background (EVR1-4, EVR1-5, and EVR1-6) at 14 (white bar) and 21 (grey bar) dpi. The total number of rosette leaves and number of rosette leaves that showed *Verticillium* symptoms was counted at least from eight plants and percentage of the disease leaves were calculated as an indication of disease severity. The bars represent averages of three independent experiments with standard deviation and asterisks indicate significance differences (Dunnett t-test at P=0.05).

FIG. 13. Relative quantification (RQ) of EVR1 transcription in wild-type (Ws) and activation-tagged mutants (A1-A4). Bars represent averages with standard deviation of three biological replicates.

FIG. 14. Transcriptional regulation of EVR1 gene during *Verticillium* infection. Relative quantification of EVR1 transcription levels in the wild-type Ws (white bar) and Col-0 (grey bar) plants at 0 (before inoculation), 4, 8, 12, and 17 days post *Verticillium* inoculation. The bars represent average and standard deviation of three technical replicates. Representative of three independent experimental replicates is shown.

FIG. 15. EVR1-over-expression alters *Arabidopsis* leaf morphology when compared to the wild-type (Col-0).

FIG. 16. Relative quantification of EVR1 transcription in the root and shoot of non-inoculated wild-type (Ws) (white bar), the activation-tagged mutant A2 (light grey bar) and EVR1 over-expressing line (EVR1-4) (dark grey bar). The EVR1 transcript level in the shoot of Ws is set at one and used for calibration. A representative of two independent biological replications is shown and bar indicates average of three technical replicates and standard deviation.

DETAILED DESCRIPTION

In the following description and examples a number of terms are used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs.

As used herein, the term "plant or part thereof" means any complete or partial plant, single cells and cell tissues such as plant cells that are intact in plants, cell clumps and tissue cultures from which plants can be regenerated. Examples of plant parts include, but are not limited to, single cells and tissues from pollen, ovules, leaves, embryos, roots, root tips, anthers, flowers, fruits, stems shoots, tubers, including potato tubers for consumption or 'seed tubers' for cultivation or clonal propagation, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "variety" is as defined in the UPOV treaty and refers to any plant grouping within a single botanical taxon of the lowest known rank, which grouping can be: (a) defined by the expression of the characteristics that results from a given genotype or combination of genotypes, (b) distinguished from any other plant grouping by the expression of at least one of the said characteristics, and (c) considered as a unit with regard to its suitability for being propagated unchanged.

The term "cultivar" (for cultivated variety) as used herein is defined as a variety that is not normally found in nature but that has been cultivated by humans, i.e. having a biological status other than a "wild" status, which "wild" status indicates the original non-cultivated, or natural state of a plant or accession. The term "cultivar" further includes, but is not limited to, semi-natural, semi-wild, weedy, traditional cultivar, landrace, breeding material, research material, breeder's lines, synthetic population, hybrid, founder stock/base population, inbred line (parent of hybrid cultivar), segregating population, mutant/genetic stock, and advanced/improved cultivar.

As used herein, "crossing" means the fertilization of female plants (or gametes) by male plants (or gametes). The term "gamete" refers to the haploid or diploid reproductive cell (egg or sperm) produced in plants by meiosis, or by first or second restitution, or double reduction from a gametophyte and involved in sexual reproduction, during which two gametes of opposite sex fuse to form a diploid or polyploid zygote. The term generally includes reference to pollen (including the sperm cell) and an ovule (including the ovum). "Crossing" therefore generally refers to the fertilization of ovules of one individual with pollen from another individual, whereas "selfing" refers to the fertilization of ovules of an individual with pollen from genetically the same individual.

The term "backcrossing" as used herein means the process wherein the plant resulting from a cross between two parental lines is crossed with one of its parental lines, wherein the parental line used in the backcross is referred to as the recurrent parent. Repeated backcrossing results in the genome becoming more and more similar to the recurrent parent, as far as this can be achieved given the level of homo- or heterozygosity of said parent.

As used herein, "selfing" is defined as refers to the process of self-fertilization wherein an individual is pollinated or fertilized with its own pollen.

The term "marker" as used herein means any indicator that is used in methods for inferring differences in characteristics of genomic sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

As used herein, "locus" is defined as the genetic or physical position that a given gene occupies on a chromosome of a plant.

The term "allele(s)" as used herein means any of one or more alternative forms of a gene, all of which alleles relate to the presence or absence of a particular phenotypic trait or characteristic in a plant. In a diploid cell or organism, the two alleles of a given gene occupy corresponding loci on a pair of homologous chromosomes. It is in some instance more accurate to refer to "haplotypes" (i.e. an allele of a chromosomal segment) in stead of "allele", however, in these instances, the term "allele" should be understood to comprise the term "haplotype".

The term "heterozygous" as used herein, and confined to diploids, means a genetic condition existing when different alleles reside at corresponding loci on homologous chromosomes.

As used herein, and confined to diploids, "homozygous" is defined as a genetic condition existing when identical alleles reside at corresponding loci on homologous chromosomes.

As used herein, and confined to multiploids, the term "nulliplex", "simplex", "duplex", "triplex", "quadruplex" and up to "multiplex", is defined as a genetic condition existing when a specific allele at a corresponding locus on corresponding homologous chromosomes is present 0, 1, 2, 3, 4 or n times, wherein n is the number of chromosomes, respectively. At the tetraploid level the phenotypic effect associated with a recessive allele is only observed when the allele is present in quadruplex condition, whereas the phenotypic effect associated with a dominant allele is already observed when the allele is present in a simplex or higher condition.

The terms "haploid", "diploid", "tetraploid" and "multiploid" as used herein are defined as having respectively one, two, four or a not further determined multiple pairs of each chromosome in each cell (excluding reproductive cells).

The term "haplotype" as used herein means a combination of alleles at multiple loci that are transmitted together on the same chromosome. This includes haplotypes referring to as few as two loci, and haplotypes referring to an entire chromosome depending on the number of recombination events that have occurred between a given set of loci.

As used herein, the term "infer" or "inferring", when used in reference to assessing the presence of the fungal resistance as related to the expression of the EVR1 gene, means drawing a conclusion about the presence of said gene in a plant or part thereof using a process of analyzing individually or in combination nucleotide occurrence(s) of said gene in a nucleic acid sample of the plant or part thereof. As disclosed herein, the nucleotide occurrence(s) can be further identified directly by examining the qualitative differences or quantitative differences in expression levels of nucleic acid molecules, or indirectly by examining (the expression level of) a the EVR1 protein.

The term "primer" as used herein refers to an oligonucleotide which is capable of annealing to the amplification target allowing a DNA polymerase to attach thereby serving as a point of initiation of DNA synthesis when placed under conditions in which synthesis of primer extension product which is complementary to a nucleic acid strand is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and source of primer. A "pair of bi-directional primers" as used herein refers to one forward and one reverse primer as commonly used in the art of DNA amplification such as in PCR amplification.

As used herein, the term "probe" means a single-stranded oligonucleotide sequence that will recognize and form a hydrogen-bonded duplex with a complementary sequence in a target nucleic acid sequence analyte or its cDNA derivative.

The terms "stringency" or "stringent hybridization conditions" refer to hybridization conditions that affect the stability of hybrids, e.g., temperature, salt concentration, pH, formamide concentration and the like. These conditions are empirically optimised to maximize specific binding and minimize non-specific binding of primer or probe to its target nucleic acid sequence. The terms as used include reference to conditions under which a probe or primer will hybridise to its target sequence, to a detectably greater degree than other sequences (e.g. at least 2-fold over background). Stringent conditions are sequence dependent and will be different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridises to a perfectly matched probe or primer.

Typically, stringent conditions will be those in which the salt concentration is less than about 1.0 M Na+ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1 M NaCl, 1% SDS at 37° C., and a wash in 0.1×SSC at 60° C. Hybridization procedures are well known in the art and are described in e.g. Ausubel, F. M., Brent, R., Kingston, R. E., Moore, D. D., Seidman, J. G., Smith, J. A., Struhl, K. eds. (1998) Current protocols in molecular biology. V. B. Chanda, series ed. New York: John Wiley & Sons.

The present invention describes the cloning of the EVR1 gene that has been found with transposon-based activation tagging. Four activation-tagged *Arabidopsis* mutants that displayed resistance to *Verticillium* wilt disease, and especially one of these that also displayed resistance to the bacterial vascular wilt pathogen *Ralstonia solanacearum* were used to determine the genetic cause of this resistance. Further, several EVR1-genes from closely related Brassicaceae species were inspected and appeared to be highly homologous to the tagged gene.

In a first embodiment, the invention provides an isolated or recombinant nucleic acid sequence comprising a nucleic acid sequence encoding the amino acid sequence EVR1 as presented in FIG. 2A or a functional fragment or a functional homologue thereof, i.e. a functional fragment or a functional homologue of the amino sequence as shown in FIG. 2A.

The term "nucleic acid" means a single or double stranded DNA or RNA molecule.

Also included are the complementary sequences of the herein described nucleotide sequences.

The term "functional fragment thereof" is typically used to refer to a fragment of the EVR1 protein that is capable of providing at least partial resistance or increasing resistance in a plant against a fungal or bacterial infection.

The term "functional homologue" is typically used to refer to a protein sequence that is highly homologous to or has a high identity with the herein described EVR1 protein, which protein is capable of providing at least partial resistance or increasing resistance in a plant against a fungal or bacterial infection, preferably an infection caused by *Verticillium*, *Fusarium* or *Ralstonia*. Included are artificial changes or amino acid residue substitutions that at least partly maintain the effect of the EVR1 protein. For example, certain amino acid residues can conventionally be replaced by others of comparable nature, e.g. a basic residue by another basic residue, an acidic residue by another acidic residue, a hydrophobic residue by another hydrophobic residue, and so on. Examples of hydrophobic amino acids are valine, leucine and isoleucine. Phenylalanine, tyrosine and tryptophan are examples of amino acids with an aromatic side chain and cysteine as well as methionine are examples of amino acids with sulphur-containing side chains. Serine and threonine contain aliphatic hydroxyl groups and are considered to be hydrophilic. Aspartic acid and glutamic acid are examples of amino acids with an acidic side chain. In short, the term "functional homologue thereof" includes variants of the EVR1 protein in which amino acids have been inserted, replaced or deleted and which at least partly maintain the effect of the EVR1 protein (i.e. at least partly providing or increasing resistance in a plant against a fungal or bacterial infection). Preferred variants are variants which only contain conventional amino acid replacements as described above. A high identity in the definition as mentioned above means an identity of at least 80, 85 or 90%. Even more preferred are amino acids that have an identity of 91, 92, 93, 94 or 95%. Most preferred are amino acids that have an identity of 96, 97, 98 or 99% with the amino acid sequence of EVR1. Homologous proteins are for example the sequences encoded by the nucleic acids other than the *Arabidopsis* nucleic acid that are shown in FIG. 7.

A functional homologous nucleic acid sequence is a nucleic acid sequence that encodes a functional homologous protein as described above. A functional fragment of a nucleotide sequence is defined as a nucleotide sequence that encodes for a functional amino acid sequence as defined above.

Homology and/or identity percentages can for example be determined by using computer programs such as BLAST, ClustalW or ClustalX.

Many nucleic acid sequences code for a protein that is 100% identical to the EVR1 protein as presented in FIG. 2A. This is because nucleotides in a nucleotide triplet may vary without changing the corresponding amino acid (wobble in the nucleotide triplets). Thus, without having an effect on the amino acid sequence of a protein the nucleotide sequence coding for this protein can be varied. However, in a preferred embodiment, the invention provides an isolated or recombinant nucleic acid sequence as depicted in FIG. 2B. In a preferred embodiment, the invention provides an isolated, synthetic, or recombinant nucleic acid that represents the coding sequence (CDS) of the EVR1 protein, i.e. the nucleotide sequence depicted in FIG. 2B or a functional fragment or a functional homologue thereof. The nucleotide sequences of homologues with a high identity are represented in FIG. 7.

Fragments as well as homologues of the herein described EVR1 gene and protein can for example be tested for their functionality by using an *Agrobacterium tumefaciens* transient transformation assay (agro-infiltration) and/or by using a detached leaf assay.

Such an assay can be performed by a functional screen for testing candidate genes using agro-infiltration, whereby 4 week old wild type *Arabidopsis thaliana* plants are infiltrated with *Agrobacterium* strains containing the candidate EVR1 homologues. The infiltrated leaves are subsequently challenged one day after infiltration with a *Verticillium* strain that is virulent on *Arabidopsis*, for example *Verticillium*

*dahliae*, in detached leaf assays. This system is equally suitable for testing candidate homologous fragments of EVR1. A person skilled in the art thus can easily determine whether or not an EVR1 homolog or fragment can be considered to be a functional homolog or fragment.

Transient gene expression, as is achieved through agroinfiltration, is a fast, flexible and reproducible approach to high-level expression of useful proteins. In plants, recombinant strains of *Agrobacterium tumefaciens* can be used for transient expression of genes that have been inserted into the T-DNA region of the bacterial Ti plasmid. A bacterial culture is infiltrated into leaves, and upon T-DNA transfer, there is ectopic expression of the gene of interest in the plant cells. However, the utility of the system is limited because the ectopic RNA expression ceases after 2-3 days. It is shown that post-transcriptional gene silencing (PTGS) is a major cause for this lack of efficiency. A system based on co-expression of a viral-encoded suppressor of gene silencing, the p19 protein of tomato bushy stunt virus (TBSV), prevents the onset of PTGS in the infiltrated tissues and allows high level of transient expression. Expression of a range of proteins was enhanced 50-fold or more in the presence of p19 so that protein purification could be achieved from as little as 100 mg of infiltrated leaf material. Although it is clear that the use of p19 has advantages, an agroinfiltration without p19 can also be used to test the functionality of candidate fragments and functional homologues.

Alternatively, each candidate nucleotide sequence (for example being a fragment or homologue) construct is targeted for transformation to a plant that is susceptible for *Verticillium*, preferably a Brassicaceae plant, more preferably *Arabidopsis*, most preferably *A. thaliana* Col-0 or Ws ecotype. Primary transformants are challenged by inoculation with *Verticillium dahliae*. Transformants that are resistant to these isolates harbour for example functional fragments or homologues of EVR1.

In yet another embodiment, the invention provides a vector comprising a nucleic acid as provided herein, i.e. a nucleic acid capable of providing at least partial resistance or increasing resistance in a plant, particularly a plant of the Brassicaceae family against a fungal or bacterial infection, more particularly against an infection with *Verticillium, Fusarium* or *Ralstonia*. More particularly, the invention provides a vector comprising an isolated, synthetic or recombinant nucleic acid sequence comprising a nucleic acid sequence encoding the amino acid sequence EVR1 of FIG. 2A or a functional fragment or a functional homologue thereof. Preferably, the invention provides a vector comprising a nucleic acid sequence as depicted in FIG. 2B.

Examples of a suitable vector are pBeloBACII, pBINplus, pKGW-MG or any commercially available (binary) cloning vector.

As will be outlined below there are multiple ways in which a nucleic acid of the invention can be transferred to a plant. One suitable means of transfer is mediated by *Agrobacterium* in which the nucleic acid to be transferred is part of a binary vector and hence it is preferred that the above described vector is a binary vector. Also suitable are other transgenic approaches, such as particle bombardment or naked DNA transfer. These alternatives are well known to the skilled person.

Another suitable means is by crossing a plant which contains the gene encoding EVR1 to a plant that does not contain the gene and to identify those progeny of the cross that have inherited the EVR1 gene.

The invention further provides a host cell comprising a nucleic acid as described herein or a vector as described herein. Examples of a preferred host cell are an *E. coli* cell suitable for BAC clones (e.g. DH10B) or an *Agrobacterium* (host) cell. In another embodiment, said host cell comprises a plant cell. A preferred plant cell is a cell derived from a member of the Brassicaceae or the Solanaceae family. From such a cell, a transgenic or genetically modified plant (for example a canola, potato or tomato plant) can be obtained by methods known by the skilled person (for example regeneration protocols).

The invention further provides a leaf, tuber, fruit or seed or other plant part or the progeny of a genetically modified plant as described herein, wherein the cells of said plant part of progeny still contain the nucleotide sequence of the invention.

In yet another embodiment, the invention provides a protein encoded by the herein described isolated or recombinant nucleic acid or a functional fragment or a functional homologue thereof. In a preferred embodiment, the invention provides a protein encoded by a nucleic acid sequence as depicted in FIG. 2B. In yet another preferred embodiment, the invention provides a protein comprising the amino acid sequence of FIG. 2A or a functional fragment or a functional homologue thereof. Further preferred are the functional (active) proteins encoded by the nucleotide sequences depicted in FIG. 7, more specifically the proteins encoded by the homologous sequences found in *Arabidopsis lyrata* (AEVR1), *Brassica oleracea* var. *gemmifera* (Bo-EVR1), and *Sisymbrium irio* (SiEVR1).

The herein described EVR1 protein comprises 70 amino acids and does not reveal any known domains that are connected with pathogen resistance. The presence of an N-terminal signal peptide, an overall net positive charge (+2), and a relatively high number of hydrophobic amino acids (28%) are typical features that are shared with many antimicrobial peptides (AMPs). In plants, six different AMPs families have been described, comprising thionins, defensins, lipid transfer proteins, knottins, heveins, and snakins, of which defensins are the largest group and best characterised (Hancock and Diamond, 2000; Thomma et al., 2002; Wang and Wang, 2004; Brown and Hancock, 2006). In *Arabidopsis*, 825 small cysteine-rich proteins with typical features of antimicrobial peptides have been predicted (Silverstein et al., 2007). Several lines of evidence indicate that AMPs play role in plant defence against viral, bacterial and fungal pathogens (Hancock and Diamond, 2000; Thomma et al., 2002; Wang and Wang, 2004; Brown and Hancock, 2006; Hancock and Sahl, 2006). AMPs are expressed in plants both constitutively and in response to pathogen attack (Garcia-Olmedo et al., 1998; Thomma et al., 2002). It has been shown that constitutive over-expression of AMPs increases plant defence against bacterial and fungal pathogens.

Vascular wilt symptoms such as wilting, stunting, chlorosis and leaf defoliation are similar to those symptoms caused by drought stress. Indeed, the physical presence of vascular wilt pathogens in the xylem vessels, enzymes secreted by the fungus or plant defence responses may interfere with water transport in the xylem (Cirulli et al., 2010). In potato, it has been shown that *Verticillium* resistant potato cultivars also show drought stress tolerance (Arbogast et al., 1999). We observed that EVR1 over-expressing plants similarly show drought stress tolerance. Leaf morphology such as size, thickness and shape has direct implication on water loss through transpiration (Khurana et al., 2008; Yang et al., 2011). EVR1 over-expressing plants have a smaller leaf size; have thicker and curly leaves than wild-type plants, which all can contribute to the amount of water loss through transpiration.

As already described, a functional fragment or a functional homologue of EVR1 is a fragment or homologue that is capable of providing at least partial resistance or increasing resistance in a plant against a fungal or bacterial infection, more particularly, an infection of *Verticillium, Fusarium* or *Ralstonia*.

Means to test the functionality of a functional fragment or a functional homologue of EVR1 have been provided above.

Based on the herein described nucleic acid sequences, the invention also provides probes and primers (i.e. oligonucleotide sequences complementary to one of the (complementary) DNA strands as described herein). Probes are for example useful in Southern or northern analysis and primers are for example useful in PCR analysis. Primers based on the herein described nucleic acid sequences are very useful to assist plant breeders active in the field of classical breeding and/or breeding by genetic modification of the nucleic acid content of a plant (preferably said plant is a Brassicaceae plant) in selecting a plant that is capable of expressing for example EVR1 or a functional fragment or functional homolog thereof.

Hence, in a further embodiment, the invention provides a binding molecule capable of binding to a nucleic acid encoding EVR1 or a functional fragment or functional homolog thereof as described herein or its complementary nucleic acid. In a preferred embodiment, said binding molecule is a primer or a probe. As mentioned, such a binding molecule is very useful for plant breeders and hence the invention further provides a method for selecting a plant or plant material or progeny thereof for its susceptibility or resistance to fungal or bacterial infection. Preferably, the nucleic acid of a plant to be tested is isolated from said plant and the obtained isolated nucleic acid is brought in contact with one or multiple (preferably different) binding molecule(s). One can for example use a PCR analysis to test plants for the presence of absence of EVR1 in the plant genome. Such a method would be especially preferable in marker-free transformation protocols, such as described in WO 03/010319.

The herein described EVR1 protein can also be used to elicit antibodies by means known to the skilled person. The invention thus also provides an antibody that (specifically) binds to the protein encoded by the herein described isolated or recombinant nucleic acid (for example the nucleic acid sequence of FIG. 2B) or an antibody that (specifically) binds to a protein as depicted in FIG. 2A or a functional fragment or a functional homolog thereof. Such an antibody is for example useful in protein analysis methods such as Western blotting or ELISA, and hence can be used in selecting plants that successfully express the EVR1 gene.

Based on the herein provided nucleic acid sequences, the invention also provides the means to introduce or increase resistance against a fungal or bacterial infection in a plant, more particularly infection with *Verticillium*, specifically *V. dahliae, V. albo-atrum* or *V. longisporum, Fusarium*, more particularly *F. oxysporum*, and *Ralstonia*, more particularly *R. solanocearum*. The invention therefore also provides a method for providing at least partial resistance or increasing resistance in a plant against a fungal or bacterial infection comprising providing a plant or a part thereof with:
   an isolated or recombinant nucleic acid sequence comprising a nucleic acid sequence encoding the EVR1 amino acid sequence of FIG. 2A or a functional fragment or a functional homologue thereof, or
   an isolated or recombinant nucleic acid sequence as depicted in FIG. 2B, or
   a vector comprising the herein described nucleic acid sequences, or
   a host cell as described herein.

Such a method for providing at least partial resistance or increasing resistance in a plant against a fungal or bacterial infection may be based on classical breeding, departing from a parent plant that already contains the EVR1 gene or a functional homolog thereof, or it involves the transfer of DNA into a plant, i.e., involves a method for transforming a plant cell comprising providing said plant cell with a nucleic acid as described herein or a vector as described herein or a host cell as described herein.

Further, the invention comprises a method of conferring drought resistance to a plant by providing said plant with:
   an isolated or recombinant nucleic acid sequence comprising a nucleic acid sequence encoding the EVR1 amino acid sequence of FIG. 2A or a functional fragment or a functional homologue thereof, or
   an isolated or recombinant nucleic acid sequence as depicted in FIG. 2B, or
   a vector comprising the herein described nucleic acid sequences, or
   a host cell as described herein.

There are multiple ways in which a recombinant nucleic acid can be transferred to a plant cell, for example *Agrobacterium* mediated transformation. However, besides by *Agrobacterium* infection, there are other means to effectively deliver DNA to recipient plant cells when one wishes to practice the invention. Suitable methods for delivering DNA to plant cells are believed to include virtually any method by which DNA can be introduced into a cell, such as by direct delivery of DNA such as by PEG-mediated transformation of protoplasts, by desiccation/inhibition-mediated DNA uptake (Potrykus et al., Mol. Gen. Genet., 199:183-188, 1985), by electroporation (U.S. Pat. No. 5,384,253), by agitation with silicon carbide fibers (Kaeppler et al., 1990; U.S. Pat. No. 5,302,523; and U.S. Pat. No. 5,464,765), and by acceleration of DNA coated particles (U.S. Pat. No. 5,550,318; U.S. Pat. No. 5,538,877; and U.S. Pat. No. 5,538,880). Through the application of techniques such as these, cells from virtually any plant species may be stably transformed, and these cells may be developed into transgenic plants.

In case *Agrobacterium* mediated transfer is used, it is preferred to use a substantially virulent *Agrobacterium* such as *A. tumefaciens*, as exemplified by strain A281 or a strain derived thereof or another virulent strain available in the art. These *Agrobacterium* strains carry a DNA region originating from the virulence region of the Ti plasmid pTiBo542, which coordinates the processing of the T-DNA and its transfer into plant cells. *Agrobacterium*-based plant transformation is well known in the art (as e.g. described in, for example by Komari, T. et al.: Plant Transformation Technology: *Agrobacterium*-Mediated Transformation, in: Handbook of Plant Biotechnology, Eds. Christou, P. and Klee, H., John Wiley & Sons, Ltd, Chichester, UK 2004, pp. 233-262). Preferably a marker-free transformation protocol is used, such as described in WO 03/010319.

Alternatively, the nucleic acid of the EVR1 gene or a functional homolog thereof may be introduced into a plant by crossing. Such a crossing scheme starts off with the selection of a suitable parent plant. This may for instance be an original *Brassica* variety or a plant that has obtained the desired nucleic acid by genetic engineering as described above.

Any suitable method known in the art for crossing selected plants may be applied in the method according to the invention. This includes both in vivo and in vitro methods. A person skilled in the art will appreciate that in vitro techniques such as protoplast fusion or embryo rescue may be applied when deemed suitable.

Selected plants that are used for crossing purposes in the methods according to the invention may have any type of ploidy. However, only plants with the same ploidy level can be crossed. Methods for increasing the ploidy of a plant are well known in the art and can be readily applied by a person skilled in the art. For example, ploidy of a diploid plant for crossing purposes can be increased by using 2N gametes of said diploid plant. Ploidy can also be increased by inhibiting chromosome segregation during meiosis, for example by treating a diploid plant with colchicine. By applying such methods on a diploid plant, embryos or gametes are obtained that comprise double the usual number of chromosomes. Such embryos or gametes can then be used for crossing purposes. In the same way also hexaploid and octaploid plants can be made. For potatoes a resistant tetraploid plant is preferred, since tetraploid plants are known to have higher yields of tubers.

Since the resistance characteristic has appeared to be a dominant trait, it is sufficient if only one allele with the functional gene is present.

Preferably, selected plants are crossed with each other using classical in vivo crossing methods that comprise one or more crossing steps including selfing. By applying such classical crossing steps characteristics of both the parents can be combined in the progeny. For example, a plant that provides a high yield can be crossed with a plant that contains large amounts of a certain nutrient. Such a crossing would provide progeny comprising both characteristics, i.e. plants that not only comprise large amounts of the nutrient but also provide high yields.

When applying backcrossing, F1 progeny is crossed with one of its high-yielding parents P to ensure that the characteristics of the F2 progeny resemble those of the high-yielding parent. Selected plants, either parent or progeny, are then crossed with themselves to produce inbred varieties for breeding. For example, selected specimens from the above mentioned F1 progeny are crossed with themselves to provide an F2 progeny from which specimens can be selected that have an increased level of resistance.

After transfer of a nucleic acid into a plant or plant cell, it must be determined which plants or plant cells have been provided with said nucleic acid. When selecting and crossing a parental genotype in a method according to the invention, a marker is used to assist selection in at least one selection step. It is known in the art that markers, indicative for a certain trait or condition, can be found in vivo and in vitro at different biological levels. For example, markers can be found at peptide level or at gene level. At gene level, a marker can be detected at RNA level or DNA level. Preferably, in the present invention the presence of such a marker is detected at DNA level, using the above described primers and/or probes. Alternatively, proper expression of the EVR1 protein or a functional homolog thereof can be assessed in plant parts by performing an immunoassay with an antibody that specifically binds the protein. Next to the primers and probes according to the invention, use can also be made of specific markers that are to be found in the vicinity of the coding sequence.

In case of transgenic approaches selecting a transformed plant may be accomplished by using a selectable marker or a reporter gene. Among the selective markers or selection genes that are most widely used in plant transformation are the bacterial neomycin phosphotransferase genes (nptI, nptII and nptIII genes) conferring resistance to the selective agent kanamycin, suggested in EP131623 and the bacterial aphIV gene suggested in EP186425 conferring resistance to hygromycin. EP 275957 discloses the use of an acetyl transferase gene from *Streptomyces viridochromogenes* that confers resistance to the herbicide phosphinotricin. Plant genes conferring relative resistance to the herbicide glyphosate are suggested in EP218571. Suitable examples of reporter genes are beta-glucuronidase (GUS), beta-galactosidase, luciferase and green fluorescent protein (GFP).

In a preferred embodiment, the invention provides a method for providing at least partial resistance or increasing resistance in a plant against infection with *Verticillium, Fusarium* and/or *Ralstonia*, more particularly. *V. dahliae, F. oxysporum* and/or *R. solanacearum*, comprising providing a plant or a part thereof with:

an isolated or recombinant nucleic acid sequence comprising a nucleic acid sequence encoding the EVR1 amino acid sequence of FIG. 2A or a functional fragment or a functional homologue thereof, or an isolated or recombinant nucleic acid sequence as depicted in FIG. 2B, or a vector comprising the herein described nucleic acid sequences, or a host cell as described herein, preferably wherein said plant comprises a plant from the Brassicaceae or Solanaceae family, preferably a *Brassica*, potato or tomato plant.

The invention also provides a plant that is obtainable by using a method for providing at least partial resistance or increasing resistance in a plant against infection with *Verticillium, Fusarium* and/or *Ralstonia*.

A preferred plant is a plant from the Brassicaceae or Solanaceae family. Many plants that are regularly cultured as crops fall within these families, such as rapeseed, canola, mustard, cauliflower, broccoli, cabbage, Brussels sprouts, rucola, cress, (horse)radish, potato, tomato, tomatillo, tobacco, bell pepper, chilli pepper, antroewa, eggplant, etc. The invention thus also provides a plant that has been provided with a nucleic acid encoding en EVR1 protein or a functional fragment or a functional homologue thereof.

The invention further provides a plant part or progeny of a plant according to the invention comprising a nucleic acid encoding the EVR1 amino acid sequence of FIG. 2A or a functional fragment or a functional homologue thereof.

The invention further provides use of an isolated or recombinant nucleic acid sequence comprising a nucleic acid sequence encoding the EVR1 amino acid sequence of FIG. 2A or a functional fragment or a functional homologue thereof or use of an isolated or recombinant nucleic acid sequence as depicted in FIG. 2B or use of a vector comprising any of said nucleic acid sequences or use of a host cell comprising any of said nucleic acid sequences or said vector for providing a plant with at least partial resistance against pathogen infection. In a preferred embodiment, said pathogen infection comprises infection with *Verticillium, Fusarium* or *Ralstonia*.

In yet another embodiment, the invention provides a method for producing EVR1 protein or a functional fragment or a functional homologue thereof comprising functionally linking a nucleic acid as described herein to a regulatory sequence and allowing said nucleic acid to be expressed in a host cell. Examples of a regulatory sequence are a promoter and/or terminator sequence. Further, it is preferred that the EVR1 sequence is expressed under control of its own promoter and terminator. The skilled person is very well capable of cloning (part of) said regulatory sequences and testing their efficiency in transcription. It is further submitted that preferably a truncated promoter, i.e. a promoter containing less than 1000, preferably not more than 900 base pairs upstream of the gene sequence, is used.

Alternatively, the gene encoding the EVR1 protein is placed under the control of a pathogen-inducible promoter. Pathogen-inducible promoters are known in the art and are responsive to a large number of pathogens and to aspecific elicitors produced by these pathogens. Examples of such pathogen inducible promoters are: the prp1 promoter (Martini, N., et al., Mol. Gen. Genet. 236, 179-186, 1993), the Fis1 promoter (WO 96/34949), the Bet v 1 promoter (Swoboda, I., et al., Plant, Cell and Env. 18, 865-874, 1995), the Vst1 promoter (Fischer, R., Dissertation, Univ. of Hohenheim, 1994; Schubert, R., et al. Plant Mol. Biol. 34, 417-426, 1997), the sesquiterpene cyclase promoter (Yin, S., et al., Plant Physiol. 115, 437-451, 1997), the MS-59 promoter (WO 99/50428), the ICS promoter from *Catharantus roseus* (WO 99/50423), the #488 promoter from *Arabidopsis thaliana* (WO 00/60086) and the gstA1 promoter (Mauch, F. and Dudler, R., Plant Physiol. 102, 1193-1201, 1993). Several other promoters are known in the art and can be used to drive expression of the nucleotide sequences of this invention.

The invention will be explained in more detail in the following, non-limiting examples.

EXAMPLES

Cultivation of Plants and Microorganisms.

*Arabidopsis thaliana* plants were soil-grown in either the greenhouse or a growth chamber. In the greenhouse, the conditions were 21 and 19° C. during the 16-h day and 8-h night period, respectively; 70% relative humidity (RH); and 100 W/m² supplemental light when the intensity dropped below 150 W/m². In the climate chamber, the conditions were 21 and 19° C. during the 14-h day and 10-h night period, respectively; 70% RH; and a light intensity of 150 W/m2.

*Verticillium* spp. and *Alternaria brassicicola* were cultivated on potato dextrose agar, *B. cinerea* and *P. cucumerina* on malt extract agar, and *F. oxysporum* f. sp. *raphani* on Czapek-Dox agar, all at room temperature. *Pseudomonas syringae* pv. *Tomato* DC3000 and *R. solanacearum* strains were cultivated as described (Deslandes et al. 1998; van Esse et al. 2008).

Plant Inoculations

*Verticillium* inoculations were performed as previously described (Ellendorff et al. 2009; van Esse et al. 2008) with the modification that roots were dipped in the conidial suspension for 5 min. *F. oxysporum* f. sp. *raphani* budcell inoculum was prepared as described (Diener and Ausubel 2005), and inoculation was performed as with *Verticillium* spp. Inoculations with *B. cinerea*, *Plectosphaerella cucumerina* (both at 106 conidia/ml), and *Pseudomonas syringae* p. v. tomato DC3000 were performed as previously described (van Esse et al. 2008). *A. brassicicola* was inoculated as with *Plectosphaerella cucumerina*. At 3 and 5 dpi, pictures were taken of all inoculated plants and lesion diameters were measured using ImageJ software. Inoculation with *R. solanacearum* was performed as described (Deslandes et al. 1998).

Determination of the Activation-Tag Insertion Site

The activation-tag insertion site in mutant A2 (the mutant *Arabidopsis* plant as identified and defined in Yadeta et al. 2011) was determined using thermal asymmetric interlaced PCR (TAIL-PCR) (Liu and Whittier, 1995). The PCR was performed with a combination of nested primers (Marsch-Martinez et al., 2002) and 10-mer random primers (Terauchi and Kahl, 2000). The secondary and tertiary TAIL-PCRs were separated on 1.2% agarose gel, stained with ethidium bromide, and visualized using the ChemiDoc XRS system (Bio-Rad). Specific product, judged based on the size differences generated by the nested primers, was excised, cleaned using the QIAquick Gel Extraction Kit (QIAGEN), cloned into the pGEM-T Easy Vector (Invitrogen), and sequenced. Blastn search of the TAIR database using the PCR sequences was performed to identify the genomic insertion site. Based on the putative insertion site, the primer pair MPR15F and MPR15R were designed and used to amplify the flanking genomic region. By sequencing this region in the wild-type and the mutant A2, the exact insertion site was determined.

EVR1 Over-Expression

The EVR1 CDS was amplified with the primer pair dMRP15-F1 and dMRP15-R1 that contain BamHI and AscI restriction sites, respectively, using Pfu DNA polymerase (Promega). The amplicon was cloned into the BamHI- and AscI-pre-digested binary vector pmk40, a variant of the vector pmog800 (Honée et al., 1998; Fradin et al., 2009). The resulting P35S:EVR1 vector construct was transformed into *A. tumefaciens* strain GV3101 and eventually in to Ws and Col-0 *Arabidopsis* ecotypes using the floral dip technique (Clough and Bent, 1998).

Cloning of EVR1 Homologs

Primer pair EVR1H-BrF0 and EVR1H-BrR1 was used to amplify BoEVR1 from genomic DNA (gDNA) of *Brassica oleracea* (Brussels sprout). The PCR product was excised from the gel, cleaned (GE Healthcare) and cloned into the pGMET-easy vector (Promega) and sequenced. Based on the sequence alignment of the PCR sequence and the *B. rapa* sequence in the database, primer EVR1H-BrR3 was designed and used in combination with EVR1H-BrF0 to amplify the predicted full length CDS of BoEVR1 from *B. oleracea* cDNA. As a control, the same primer combination was used to amplify BoEVR1 from gDNA. The PCR fragments were sequenced to confirm the full length CDS. To generate an BoEVR1 over-expression construct, the full length CDS of BoEVR1 was amplified from cDNA using primer pair EVR1H-BaF1 and EVR1H-AsR1 containing BamHI and AscI custom restriction sites, respectively, and cloned into BamHI and AscI pre-digested binary vector pB7K40 (Yadeta et al., 2011). Subsequently, the binary vector construct was transformed into *A. tumefaciens* (strain GV3101) and eventually into *Arabidopsis* ecotypes Ws and Col-0.

Expression of EVR1 Homologs in *N. benthamiana*

In order to test whether expression of AtEVR1 and BoEVR1 results in *Verticillium* wilt resistance in non-Brassicaceae plants as well, the binary vectors containing AtEVR1 or BoEVR1 were transformed into *N. benthamiana*, a Solanaceae family member, following a standard *N. benthamiana* transformation protocol (Wang, 2006).

Pathogen Quantification in Planta

Real-time PCR was used for quantification of pathogen colonization in planta using an ABI7300 PCR machine (Applied Biosystems) in combination with the qPCR Core kit for SYBR Green I (Eurogentec, Maastricht, The Netherlands) and analyzed using the 7300 System SDS software (Applied Biosystems). Unless described otherwise, the primer pair AtRub-F4 and AtRub-R4 targeting the gene encoding the large subunit of RuBisCo was used as endogenous control. *Verticillium* colonization was assessed as previously described (Ellendorff et al., 2009; Yadeta et al., 2011).

Expression Analysis

Both reverse transcription PCR and real-time PCR were used to analyze gene expression. Unless described otherwise, the primer pair Act2-F2 and Act2-R2 targeting the *Arabidopsis* Actin 2 gene was used as endogenous control. A list of primers used in this study and their targets is presented in Table S1. The real-time PCR conditions consisted of 2 min incubation at 50° C. and 10 min at 95° C. followed by 40 cycles of 95° C. for 15 sec. and 60° C. for 1 min.

TABLE 1

Analysis of the genes flanking the activation-tag insertion site in mutant A2

| Gene | Annotation | Knock-out allele | Expression[1] | *Verticillium* phenotype[2] |
| --- | --- | --- | --- | --- |
| At3g13405/03 | MicroRNA | SALK_113174C | Not tested | Similar |
| At3g13410 | Unknown protein | None available | Similar | Similar |
| At3g13420 | Zinc finger family | SALK_041147C | Similar | Similar |
| At3g13430 | Zinc finger family | SALK_135697 | Similar | Similar |
| At3g13432 | Unknown protein | None available | Similar | Similar |
| At3g13435 | Unknown protein | SALK_091102 | Induced in A2 mutant | Similar |
| At3g13437 | Unknown protein | SALK_139498C | Induced in A2 mutant | Enhanced susceptibility |
| At3g13440 | Methyltransferase/nucleic acid binding protein | SALK_020621 | Similar | Similar |
| At3g13445 | TATA binding protein | SALK_084279C | Induced in A2 mutant | Similar |
| At3g13450 | Alpha-keto acid dehydrogenase E1 | SALK_042796C | Similar | Similar |
| At3g13460 | ECT2 like (Physically interacts with CIPK1) | SALK_002225C | Similar | Similar |

[1]Gene expression in mutant A2 relative to the expression in wild-type.
[2]Phenotype of knock-out alleles upon *V. dahliae* inoculation when compared to wild-type plants.

Supplementary Data

TABLE S1

Primers used in this study

| Primer code | sequence (5' to 3') | purpose |
| --- | --- | --- |
| MPR15F | ACCTTGTCTTTTGTATTCACTG (SEQ ID 7) | Confirmation of activation tag insertion site |
| MPR15R | AAGTTTGGAACGAGGCAG (SEQ ID 8) | Confirmation of activation tag insertion site |
| MPR15-F1 | GGAGTTTTGTACTTTGCGACG (SEQ ID 9) | Confirmation of activation tag insertion site |
| MPR15-R1 | AGTTTGGAACGAGCAGC (SEQ ID 10) | Confirmation of activation tag insertion site |
| dMRP15-2F1 | GCATCACATTTTCCAATTCGAC (SEQ ID 11) | AtEVR1 expression analysis (RT-PCR) |
| dMRP15-2R1 | CATTGCAACAAATCCAGC (SEQ ID 12) | AtEVR1 expression analysis (RT-PCR) |
| dMRP15-F1 | GGATCCATGAGTCTCAAGTTCATTC (SEQ ID 13) | AtEVR1 over-expression construct (BAMHI) |
| dMRP15-R1 | GGCGCGCCTTAATCATTGCAACAAATCC (SEQ ID 14) | AtEVR1 over-expression construct (AscI) |
| ITS1-F | AAAGTTTTAATGGTTCGCTAAGA (SEQ ID 15) | *Verticillium* quantification (Ellendorf et al., 2009) |
| St-Ve1-R | CTTGGTCATTTAGAGGAAGTAA (SEQ ID 16) | *Verticillium* quantification (Ellendorf et al., 2009) |
| AtRub-F4 | GCAAGTGTTGGGTTCAAAGCTGG (SEQ ID 17) | *Verticillium* quantification (Yadeta et al., 2011) |
| AtRub-R4 | AACGGGCTCGATGTGGTAGC (SEQ ID 18) | *Verticillium* quantification (Yadeta et al., 2011) |

TABLE S1-continued

Primers used in this study

| Primer code | sequence (5' to 3') | purpose |
|---|---|---|
| EVR1-F | ATGAGTCTCAAGTTCATTCTTATAGC (SEQ ID 19) | gfp fusion construct |
| EVR1-R | ATCATTGCAACAAATCCAGCC (SEQ ID 20) | gfp fusion construct |
| EVR1-F1 | GTATCACACCAACTGTAATGAGAACG (SEQ ID 21) | T-DNA insertion check |
| EVR1-R1 | TTAATCATTGCAACAAATCCAG (SEQ ID 22) | T-DNA insertion check |
| EVR1-eF1 | CGGTATGAATTCcatcatcatcatcatcatcc cgactacaaggacgacgatgacaagACCGTCG TTCCTTTTTCC (SEQ ID 23) | AtEVR1 protein expression (His6-FLAG-AtEVR1-$^{Sp}$) |
| EVR1-nR1 | CGTCTAGCGGCCGCTTAATCATTGCAACAAAT CC (SEQ ID 24) | AtEVR1 protein expression in *P. pastoris* (His6-FLAG-AtEVR1-$^{Sp}$) |
| EVR1-F2 | CGGTATGAATTCACCGTCGTTCCTTTTTCC (SEQ ID 25) | Y2H |
| EVR1-R2 | AGTCTCGTCGACTTAATCATTGCAACAAATCC (SEQ ID 26) | Y2H |
| EVR1H-BrF0 | ATGAGTCTCAAGTTCATT (SEQ ID 27) | Cloning BsEVR1 |
| EVR1H-BrR1 | CAGAGCTTCTTTTAATCATTGC (SEQ ID 28) | Cloning BsEVR1 |
| EVR1H-BrR3 | TTAATCATTGCAGCAATT (SEQ ID 29) | Cloning BsEVR1 |
| EVR1H-BaF1 | GCAGGATCCATGAGTCTCAAGTTCATT (SEQ ID 30) | Making BsEVR1 over expression construct |
| EVR1H-AsR1 | ACTGGCGCGCCTTAATCATTGCAGCAATT (SEQ ID 31) | Making BsEVR1 over expression construct |
| Act2-F2 | TAACTCTCCCGCTATGTATGTCGC (SEQ ID 32) | *Arabidopsis* act2 gene (Endogenous control) |
| Act2-R2 | GAGAGAAACCCTCGTAGATTGGC (SEQ ID 33) | *Arabidopsis* act2 gene (Endogenous control) |
| EVR1-FJ | ATACTGGATCCATGAGTCTCAAGTTCATTCTT (SEQ ID 34) | ΔAtEVR1C68C69 |
| EVR1-CC-R | TATATGGCGCGCCTTAATCATTAGCAGCAATCCAGCCTTT (SEQ ID 35) | ΔAtEVR1C68C69 |
| EVR1-AKG-R | TATATGGCGCGCCTTAATCATTGCAACAAAT CCAGCAGCTGCAGGAGGCGAACGGCT (SEQ ID 36) | ΔAtEVR1C68C69 |
| EVR1-SRSP-R | TATATGGCGCGCCTTAATCATTGCAACAAAT CCAGCCTTTTGCAGGAGCAGCAGCAGCGACTTTTACGGTGAT (SEQ ID 37) | ΔAtEVR1C68C69 |
| EVR1-VKV-R | TATATGGCGCGCCTTAATCATTGCAACAAAT CCAGCCTTTTGCAGGAGGCGAACGGCTAGC AGCAGCGGTGATCTTCTTTCCTTT (SEQ ID 38) | ΔAtEVR1C68C69 |
| AtEVR1-OLF | TGCATCACATTTTCCAATTCGATTGACATTC ACAAAGGAAAG (SEQ ID 39) | AtEVR1 truncation |
| AtEVR1-OLR | CTTTCCTTTGTGAATGTCAATCGAATTGGAA AATGTGATGCA (SEQ ID 40) | |

TABLE S1-continued

Primers used in this study

| Primer code | sequence (5' to 3') | purpose |
|---|---|---|
| AtEVR1-NtR | GGCGCGCCTTACTCTCTACCTTCTTCTTC (SEQ ID 41) | |
| dMRP15-1F1 | GAATTGGAAGTTGGTTTTGC (SEQ ID 42) | Expression analysis |
| dMRP15-1R1 | AGAAATGATCTTCGGTGG (SEQ ID 43) | Expression analysis |
| dMRP15-2F1 | GCATCACATTTTCCAATTCGAC (SEQ ID 44) | Expression analysis |
| dMRP15-2R1 | CATTGCAACAAATCCAGC (SEQ ID 45) | Expression analysis |
| dMRP15-3F1 | AGAGAGTAATCCAATGGACC (SEQ ID 46) | Expression analysis |
| dMRP15-3R1 | GATGTCTCTTTGTCCTGG (SEQ ID 47) | Expression analysis |
| dMRP15-4F1 | GATTGGAAGGGAGTAATCC (SEQ ID 48) | Expression analysis |
| dMRP15-4R1 | TCTGAATTCCGAGAGCAC (SEQ ID 49) | Expression analysis |
| uMRP15-1F1 | GTTCTGTTTGATTGCTTCCC (SEQ ID 50) | Expression analysis |
| uMRP15-1R1 | CTGAATTTGGACTTGCGG (SEQ ID 51) | Expression analysis |
| uMRP15-2F1 | CATCAGAGACTAGCTACTGG (SEQ ID 52) | Expression analysis |
| uMRP15-2R1 | GTTCGAACTTGAGTCTGG (SEQ ID 53) | Expression analysis |
| uMRP15-3F1 | GCTTTGTGTTTCGTTACG (SEQ ID 54) | Expression analysis |
| uMRP15-3R1 | AAGACCTGTGTTGCATTG (SEQ ID 55) | Expression analysis |
| uMRP15-4F1 | GTGTTTCTATCTGTGGCC (SEQ ID 56) | Expression analysis |
| uMRP15-4R1 | GAATCTTGAGGAGTCTCG (SEQ ID 57) | Expression analysis |

The invention claimed is:

1. A method for providing at least partial resistance or increasing resistance in a plant against pathogen infection, the method comprising providing a plant or a part thereof transformed with a nucleic acid encoding the amino acid sequence EVR1 of SEQ ID NO: 2 or a functional homologue thereof having at least 90% identity to SEQ ID NO: 2, resulting in increased expression of SEQ ID NO: 2, or the functional homologue thereof, over endogenous levels.

2. The method according to claim 1, wherein said pathogen infection comprises *Verticillium, Fusarium* and/or *Ralstonia* infection.

3. The method according to claim 1, wherein the functional homologue is an amino acid sequence encoded by the nucleic acid sequence of SEQ ID NOS: 3, 4, 5, or 6.

4. The method according to claim 1, wherein the nucleic acid sequence is selected from the group consisting of SEQ ID NOS: 1, 3, 4, 5, and 6.

5. A method for breeding a pathogen resistant plant, comprising:

a. providing a first plant transformed with a nucleic acid sequence encoding the amino acid sequence EVR1 of SEQ ID NO: 2 or a functional homologue thereof having at least 90% identity to SEQ ID NO: 2, wherein said step optionally comprises adapting the ploidy level of gametes of said transformed plant;

b. crossing said first plant with a second plant; and c. selecting the offspring of said cross for the presence of said nucleic acid sequence.

6. The method of claim 1 further comprising the step of selecting a plant or progeny thereof for its resistance to a pathogen infection.

7. The method of claim 1 where the plant is from the Brassicaceae or Solanaceae family.

8. The method of claim 6 further comprising the step of testing at least part of said plant or progeny thereof for the presence of said nucleic acid sequence.

* * * * *

SEQUENCE LISTING

<160> NUMBER OF SEQ ID NOS: 57

<210> SEQ ID NO 1
<211> LENGTH: 213
<212> TYPE: DNA
<213> ORGANISM: Arabidopsis thaliana
<220> FEATURE:
<221> NAME/KEY: CDS
<222> LOCATION: (1)..(213)

<400> SEQUENCE: 1

```
atg agt ctc aag ttc att ctt ata gct ttg ctt cta ctt tta tgc atc      48
Met Ser Leu Lys Phe Ile Leu Ile Ala Leu Leu Leu Leu Leu Cys Ile
1               5                   10                  15
```

| aca ttt tcc aat tcg acc gtc gtt cct ttt tcc aaa aac cgg aaa att | 96 |
| Thr Phe Ser Asn Ser Thr Val Val Pro Phe Ser Lys Asn Arg Lys Ile | |
|                   20                 25               30 | |

```
aca ttt tcc aat tcg acc gtc gtt cct ttt tcc aaa aac cgg aaa att      96
Thr Phe Ser Asn Ser Thr Val Val Pro Phe Ser Lys Asn Arg Lys Ile
             20                  25                  30 acc aat gaa gaa gaa gaa gaa ggt aga gag att gac att cac aaa         144
Thr Asn Glu Glu Glu Glu Glu Gly Arg Glu Ile Asp Ile His Lys
         35                  40                  45 gga aag aag atc acc gta aaa gtc agc cgt tcg cct cct gca aaa ggc     192
Gly Lys Lys Ile Thr Val Lys Val Ser Arg Ser Pro Pro Ala Lys Gly
     50                  55                  60 tgg att tgt tgc aat gat tga                                         213
Trp Ile Cys Cys Asn Asp
65                  70

<210> SEQ ID NO 2
<211> LENGTH: 70
<212> TYPE: PRT
<213> ORGANISM: Arabidopsis thaliana

<400> SEQUENCE: 2

Met Ser Leu Lys Phe Ile Leu Ile Ala Leu Leu Leu Leu Cys Ile
1               5                   10                  15

Thr Phe Ser Asn Ser Thr Val Val Pro Phe Ser Lys Asn Arg Lys Ile
             20                  25                  30

Thr Asn Glu Glu Glu Glu Glu Gly Arg Glu Ile Asp Ile His Lys
         35                  40                  45

Gly Lys Lys Ile Thr Val Lys Val Ser Arg Ser Pro Pro Ala Lys Gly
     50                  55                  60

Trp Ile Cys Cys Asn Asp
65                  70

<210> SEQ ID NO 3
<211> LENGTH: 201
<212> TYPE: DNA
<213> ORGANISM: Arabidopsis lyrata

<400> SEQUENCE: 3
atgagtttca agttcattct aataactatg cttatacttt tatgcatcgc atcttccaat    60
tcgaccatca ctccattttc tagaaaccga aaaattatcg ttgaagaagg tggaaagatt   120
cacatacaca agggaaagaa gatcacagta aacccagcc gttcacctcc tgcaaaaggc    180
actaaaaatt acacaacata g                                             201

<210> SEQ ID NO 4
<211> LENGTH: 204
<212> TYPE: DNA
<213> ORGANISM: Brassica oleracea

<400> SEQUENCE: 4
atgagtctca agttcattct attaacagct tcacttctac ttttatgtat cccatcttca    60
gattccacaa tcctttcatc gctcagaaac cagaaacttc tcaatgaaga agttggaaaa   120
attcacattc ataaggaaaa caagatcagc gtaaaagtca gccgttcacc tcttgccaaa   180
ggcagaaatt gctgcaatga ttaa                                          204

<210> SEQ ID NO 5
<211> LENGTH: 204
<212> TYPE: DNA
<213> ORGANISM: Brassica rapa
```

```
<400> SEQUENCE: 5
atgagtctca agttcattct attaatagct tcacttgtac ttttatgtat cgcatcgtct     60
gattcggcaa tccttccatt tctcagaaac cagaaacttc tcaatgaaga agttggaaaa    120
attcacattc acaaagaaaa caagatcagc gtaaaagtca gccgttcacc tcctgccaaa    180
ggcagaaatt gctgcaatga ttaa                                           204

<210> SEQ ID NO 6
<211> LENGTH: 208
<212> TYPE: DNA
<213> ORGANISM: Sisymbrium irio

<400> SEQUENCE: 6
atgaggctca agttcatttt attaatagct tcacttttac ttgtatgcat cgcatcttcc     60
gattcggcaa tccttccagt tttcagaaac cggaaactta gtcaatgtag gagaaggtgg    120
aaagattcac attctcaagg aaaaacagat caccgtaaac ttcagccgtt cacctcctgc    180
caaaggctgg atttgttgcg aagattaa                                       208

<210> SEQ ID NO 7
<211> LENGTH: 22
<212> TYPE: DNA
<213> ORGANISM: Artificial
<220> FEATURE:
<223> OTHER INFORMATION: primer

<400> SEQUENCE: 7
accttgtctt ttgtattcac tg                                              22

<210> SEQ ID NO 8
<211> LENGTH: 18
<212> TYPE: DNA
<213> ORGANISM: Artificial
<220> FEATURE:
<223> OTHER INFORMATION: primer

<400> SEQUENCE: 8
aagtttggaa cgaggcag                                                   18

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
ggagttttgt actttgcgac g                                               21

<210> SEQ ID NO 10
<211> LENGTH: 18
<212> TYPE: DNA
<213> ORGANISM: Artificial
<220> FEATURE:
<223> OTHER INFORMATION: primer

<400> SEQUENCE: 10
agtttggaac gaggcagc                                                   18

<210> SEQ ID NO 11
<211> LENGTH: 22
<212> TYPE: DNA
<213> ORGANISM: Artificial
```

```
<220> FEATURE:
<223> OTHER INFORMATION: primer

<400> SEQUENCE: 11
gcatcacatt ttccaattcg ac                                            22

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
cattgcaaca aatccagc                                                 18

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
ggatccatga gtctcaagtt cattc                                         25

<210> SEQ ID NO 14
<211> LENGTH: 28
<212> TYPE: DNA
<213> ORGANISM: Artificial
<220> FEATURE:
<223> OTHER INFORMATION: primer

<400> SEQUENCE: 14
ggcgcgcctt aatcattgca acaaatcc                                      28

<210> SEQ ID NO 15
<211> LENGTH: 23
<212> TYPE: DNA
<213> ORGANISM: Artificial
<220> FEATURE:
<223> OTHER INFORMATION: primer

<400> SEQUENCE: 15
aaagttttaa tggttcgcta aga                                           23

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
cttggtcatt tagaggaagt aa                                            22

<210> SEQ ID NO 17
<211> LENGTH: 23
<212> TYPE: DNA
<213> ORGANISM: Artificial
<220> FEATURE:
<223> OTHER INFORMATION: primer

<400> SEQUENCE: 17
gcaagtgttg ggttcaaagc tgg                                           23
```

-continued

```
<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
aacgggctcg atgtggtagc                                                 20

<210> SEQ ID NO 19
<211> LENGTH: 26
<212> TYPE: DNA
<213> ORGANISM: Artificial
<220> FEATURE:
<223> OTHER INFORMATION: primer

<400> SEQUENCE: 19
atgagtctca agttcattct tatagc                                          26

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
atcattgcaa caaatccagc c                                               21

<210> SEQ ID NO 21
<211> LENGTH: 26
<212> TYPE: DNA
<213> ORGANISM: Artificial
<220> FEATURE:
<223> OTHER INFORMATION: primer

<400> SEQUENCE: 21
gtatcacacc aactgtaatg agaacg                                          26

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
ttaatcattg caacaaatcc ag                                              22

<210> SEQ ID NO 23
<211> LENGTH: 75
<212> TYPE: DNA
<213> ORGANISM: Artificial
<220> FEATURE:
<223> OTHER INFORMATION: primer

<400> SEQUENCE: 23
cggtatgaat tccatcatca tcatcatcat cccgactaca aggacgacga tgacaagacc     60
gtcgttcctt tttcc                                                      75

<210> SEQ ID NO 24
<211> LENGTH: 34
<212> TYPE: DNA
<213> ORGANISM: Artificial
```

```
<220> FEATURE:
<223> OTHER INFORMATION: primer

<400> SEQUENCE: 24
cgtctagcgg ccgcttaatc attgcaacaa atcc                              34

<210> SEQ ID NO 25
<211> LENGTH: 30
<212> TYPE: DNA
<213> ORGANISM: Artificial
<220> FEATURE:
<223> OTHER INFORMATION: primer

<400> SEQUENCE: 25
cggtatgaat tcaccgtcgt tcctttttcc                                   30

<210> SEQ ID NO 26
<211> LENGTH: 32
<212> TYPE: DNA
<213> ORGANISM: Artificial
<220> FEATURE:
<223> OTHER INFORMATION: primer

<400> SEQUENCE: 26
agtctcgtcg acttaatcat tgcaacaaat cc                                32

<210> SEQ ID NO 27
<211> LENGTH: 18
<212> TYPE: DNA
<213> ORGANISM: Artificial
<220> FEATURE:
<223> OTHER INFORMATION: primer

<400> SEQUENCE: 27
atgagtctca agttcatt                                                18

<210> SEQ ID NO 28
<211> LENGTH: 22
<212> TYPE: DNA
<213> ORGANISM: Artificial
<220> FEATURE:
<223> OTHER INFORMATION: primer

<400> SEQUENCE: 28
cagagcttct tttaatcatt gc                                           22

<210> SEQ ID NO 29
<211> LENGTH: 18
<212> TYPE: DNA
<213> ORGANISM: Artificial
<220> FEATURE:
<223> OTHER INFORMATION: primer

<400> SEQUENCE: 29
ttaatcattg cagcaatt                                                18

<210> SEQ ID NO 30
<211> LENGTH: 27
<212> TYPE: DNA
<213> ORGANISM: Artificial
<220> FEATURE:
<223> OTHER INFORMATION: primer

<400> SEQUENCE: 30
gcaggatcca tgagtctcaa gttcatt                                      27
```

```
<210> SEQ ID NO 31
<211> LENGTH: 29
<212> TYPE: DNA
<213> ORGANISM: Artificial
<220> FEATURE:
<223> OTHER INFORMATION: primer

<400> SEQUENCE: 31
actggcgcgc cttaatcatt gcagcaatt                                  29

<210> SEQ ID NO 32
<211> LENGTH: 24
<212> TYPE: DNA
<213> ORGANISM: Artificial
<220> FEATURE:
<223> OTHER INFORMATION: primer

<400> SEQUENCE: 32
taactctccc gctatgtatg tcgc                                       24

<210> SEQ ID NO 33
<211> LENGTH: 23
<212> TYPE: DNA
<213> ORGANISM: Artificial
<220> FEATURE:
<223> OTHER INFORMATION: primer

<400> SEQUENCE: 33
gagagaaacc ctcgtagatt ggc                                        23

<210> SEQ ID NO 34
<211> LENGTH: 32
<212> TYPE: DNA
<213> ORGANISM: Artificial
<220> FEATURE:
<223> OTHER INFORMATION: primer

<400> SEQUENCE: 34
atactggatc catgagtctc aagttcattc tt                              32

<210> SEQ ID NO 35
<211> LENGTH: 40
<212> TYPE: DNA
<213> ORGANISM: Artificial
<220> FEATURE:
<223> OTHER INFORMATION: primer

<400> SEQUENCE: 35
tatatggcgc gccttaatca ttagcagcaa tccagccttt                      40

<210> SEQ ID NO 36
<211> LENGTH: 58
<212> TYPE: DNA
<213> ORGANISM: Artificial
<220> FEATURE:
<223> OTHER INFORMATION: primer

<400> SEQUENCE: 36
tatatggcgc gccttaatca ttgcaacaaa tccaagcagc tgcaggaggc gaacggct   58

<210> SEQ ID NO 37
<211> LENGTH: 73
<212> TYPE: DNA
<213> ORGANISM: Artificial
<220> FEATURE:
<223> OTHER INFORMATION: primer
```

<400> SEQUENCE: 37
tatatggcgc gccttaatca ttgcaacaaa tccagccttt tgcaggagca gcagcagcga    60
cttttacggt gat    73

<210> SEQ ID NO 38
<211> LENGTH: 85
<212> TYPE: DNA
<213> ORGANISM: Artificial
<220> FEATURE:
<223> OTHER INFORMATION: primer

<400> SEQUENCE: 38
tatatggcgc gccttaatca ttgcaacaaa tccagccttt tgcaggaggc gaacggctag    60
cagcagcggt gatcttcttt cctttt    85

<210> SEQ ID NO 39
<211> LENGTH: 42
<212> TYPE: DNA
<213> ORGANISM: Artificial
<220> FEATURE:
<223> OTHER INFORMATION: primer

<400> SEQUENCE: 39
tgcatcacat tttccaattc gattgacatt cacaaaggaa ag    42

<210> SEQ ID NO 40
<211> LENGTH: 42
<212> TYPE: DNA
<213> ORGANISM: Artificial
<220> FEATURE:
<223> OTHER INFORMATION: primer

<400> SEQUENCE: 40
ctttcctttg tgaatgtcaa tcgaattgga aaatgtgatg ca    42

<210> SEQ ID NO 41
<211> LENGTH: 29
<212> TYPE: DNA
<213> ORGANISM: Artificial
<220> FEATURE:
<223> OTHER INFORMATION: primer

<400> SEQUENCE: 41
ggcgcgcctt actctctacc ttcttcttc    29

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
gaattggaag ttggttttgc    20

<210> SEQ ID NO 43
<211> LENGTH: 18
<212> TYPE: DNA
<213> ORGANISM: Artificial
<220> FEATURE:
<223> OTHER INFORMATION: primer

<400> SEQUENCE: 43
agaaatgatc ttcggtgg    18

```
<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
gcatcacatt ttccaattcg ac                                             22

<210> SEQ ID NO 45
<211> LENGTH: 18
<212> TYPE: DNA
<213> ORGANISM: Artificial
<220> FEATURE:
<223> OTHER INFORMATION: primer

<400> SEQUENCE: 45
cattgcaaca aatccagc                                                  18

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
agagagtaat ccaatggacc                                                20

<210> SEQ ID NO 47
<211> LENGTH: 18
<212> TYPE: DNA
<213> ORGANISM: Artificial
<220> FEATURE:
<223> OTHER INFORMATION: primer

<400> SEQUENCE: 47
gatgtctctt tgtcctgg                                                  18

<210> SEQ ID NO 48
<211> LENGTH: 19
<212> TYPE: DNA
<213> ORGANISM: Artificial
<220> FEATURE:
<223> OTHER INFORMATION: primer

<400> SEQUENCE: 48
gattggaagg gagtaatcc                                                 19

<210> SEQ ID NO 49
<211> LENGTH: 18
<212> TYPE: DNA
<213> ORGANISM: Artificial
<220> FEATURE:
<223> OTHER INFORMATION: primer

<400> SEQUENCE: 49
tctgaattcc gagagcac                                                  18

<210> SEQ ID NO 50
<211> LENGTH: 20
<212> TYPE: DNA
<213> ORGANISM: Artificial
<220> FEATURE:
<223> OTHER INFORMATION: primer
```

```
<400> SEQUENCE: 50
gttctgtttg attgcttccc                                              20

<210> SEQ ID NO 51
<211> LENGTH: 18
<212> TYPE: DNA
<213> ORGANISM: Artificial
<220> FEATURE:
<223> OTHER INFORMATION: primer

<400> SEQUENCE: 51
ctgaatttgg acttgcgg                                                18

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
catcagagac tagctactgg                                              20

<210> SEQ ID NO 53
<211> LENGTH: 18
<212> TYPE: DNA
<213> ORGANISM: Artificial
<220> FEATURE:
<223> OTHER INFORMATION: primer

<400> SEQUENCE: 53
gttcgaactt gagtctgg                                                18

<210> SEQ ID NO 54
<211> LENGTH: 18
<212> TYPE: DNA
<213> ORGANISM: Artificial
<220> FEATURE:
<223> OTHER INFORMATION: primer

<400> SEQUENCE: 54
gctttgtgtt tcgttacg                                                18

<210> SEQ ID NO 55
<211> LENGTH: 18
<212> TYPE: DNA
<213> ORGANISM: Artificial
<220> FEATURE:
<223> OTHER INFORMATION: primer

<400> SEQUENCE: 55
aagacctgtg ttgcattg                                                18

<210> SEQ ID NO 56
<211> LENGTH: 18
<212> TYPE: DNA
<213> ORGANISM: Artificial
<220> FEATURE:
<223> OTHER INFORMATION: primer

<400> SEQUENCE: 56
gtgtttctat ctgtggcc                                                18
```

```
<210> SEQ ID NO 57
<211> LENGTH: 18
<212> TYPE: DNA
<213> ORGANISM: Artificial
<220> FEATURE:
<223> OTHER INFORMATION: primer

<400> SEQUENCE: 57
gaatcttgag gagtctcg                                                 18
```